United States Patent
Hoffmeyer et al.

(10) Patent No.: US 9,784,711 B2
(45) Date of Patent: *Oct. 10, 2017

(54) DISPOSABLE CARTRIDGE FOR MICROFLUIDICS SYSTEMS

(71) Applicant: TECAN TRADING AG, Mennedorf (CH)

(72) Inventors: Daniel Hoffmeyer, San Jose, CA (US); Tiffany Lay, San Jose, CA (US); Travis Lee, San Francisco, CA (US); Marc N. Feiglin, East Brunswick, NJ (US); Werner Halg, Mannedorf (CH); Anne R. Kopf-Sill, Portola Valley, CA (US)

(73) Assignee: TECAN TRADING AG, Mannedorf (CH)

( * ) Notice: Subject to any disclaimer, the term of this patent is extended or adjusted under 35 U.S.C. 154(b) by 337 days.

This patent is subject to a terminal disclaimer.

(21) Appl. No.: 14/402,717

(22) PCT Filed: Jan. 6, 2014

(86) PCT No.: PCT/EP2014/050086
§ 371 (c)(1),
(2) Date: Nov. 21, 2014

(87) PCT Pub. No.: WO2014/108367
PCT Pub. Date: Jul. 17, 2014

(65) Prior Publication Data
US 2015/0144489 A1    May 28, 2015

(30) Foreign Application Priority Data
Jan. 9, 2013  (WO) .................. PCT/EP2013/050326

(51) Int. Cl.
| | | |
|---|---|---|
| *G01N 27/447* | (2006.01) | |
| *B01L 3/00* | (2006.01) | |
| *B81B 1/00* | (2006.01) | |

(52) U.S. Cl.
CPC ........ *G01N 27/44791* (2013.01); *B01L 3/505* (2013.01); *B01L 3/502715* (2013.01);
(Continued)

(58) Field of Classification Search
CPC ....................... G01N 27/447–27/44795; B01D 57/00–57/02; C02F 1/4696; B81B 1/00–1/008
(Continued)

(56) References Cited

U.S. PATENT DOCUMENTS

| | | | |
|---|---|---|---|
| 9,377,439 B2* | 6/2016 | Lee ................... | G01N 27/44791 |
| 2008/0006535 A1* | 1/2008 | Paik .................. | B01L 3/502792 |
| | | | 204/600 |
| 2013/0134039 A1* | 5/2013 | Bjornson .......... | B01L 3/502715 |
| | | | 204/451 |

FOREIGN PATENT DOCUMENTS

| | | | |
|---|---|---|---|
| WO | WO 2009/137415 A2 | 11/2009 | |
| WO | WO 2010/009463 A2 | 1/2010 | |

(Continued)

OTHER PUBLICATIONS

International Search Report for PCT/EP2014/050086 filed Jan. 6, 2014.
(Continued)

*Primary Examiner* — Bach Dinh
(74) *Attorney, Agent, or Firm* — Notaro, Michalos & Zaccaria P.C.

(57) ABSTRACT

A disposable cartridge used in a digital microfluidics system has a bottom layer with first hydrophobic surface, a rigid cover plate with second hydrophobic surface, and a gap there-between. The bottom layer is a flexible film on an
(Continued)

Figure 1:
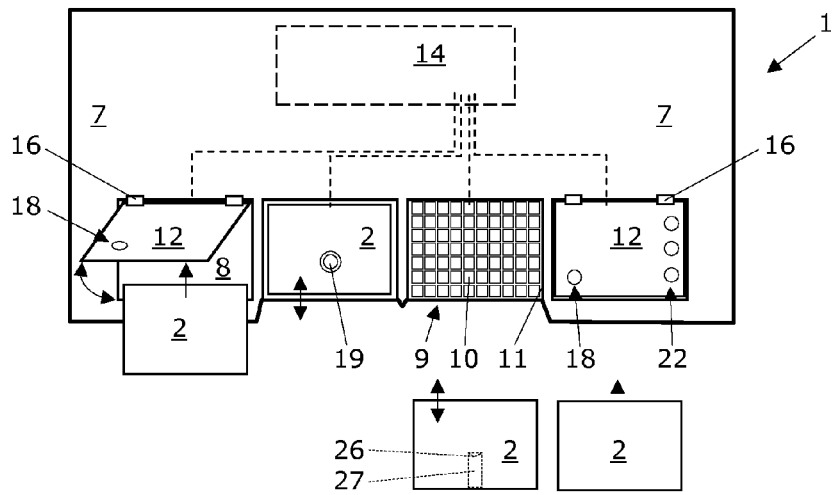

uppermost surface of a cartridge accommodation site of a system, attracted to and spread over the uppermost surface by an underpressure. A lower surface of the plate and the flexible bottom layer are sealed to each other. The assembled cartridge is removed from the cartridge accommodation site in one piece and potentially includes samples and processing fluids. The system has a base unit and a cartridge accommodation site with an electrode array of individual electrodes and a central control unit for controlling selection of individual electrodes and for providing these electrodes with individual voltage pulses for manipulating liquid droplets within the gap by electrowetting.

27 Claims, 5 Drawing Sheets

(52) U.S. Cl.
CPC .. *B01L 3/502792* (2013.01); *G01N 27/44756* (2013.01); *B01L 2200/027* (2013.01); *B01L 2200/04* (2013.01); *B01L 2300/044* (2013.01); *B01L 2300/123* (2013.01); *B01L 2400/0427* (2013.01); *B81B 1/00* (2013.01)

(58) Field of Classification Search
USPC ............... 204/450–470, 546–550, 600–621, 204/643–645
See application file for complete search history.

(56) References Cited

FOREIGN PATENT DOCUMENTS

| WO | WO 2010/069977 A1 | 6/2010 |
|----|-------------------|--------|
| WO | WO 2011/002957 A2 | 1/2011 |
| WO | WO 2013/075902 A1 | 5/2013 |

OTHER PUBLICATIONS

International Preliminary Report on Patentability for PCT/EP2014/050086 filed Jan. 6, 2014.

* cited by examiner

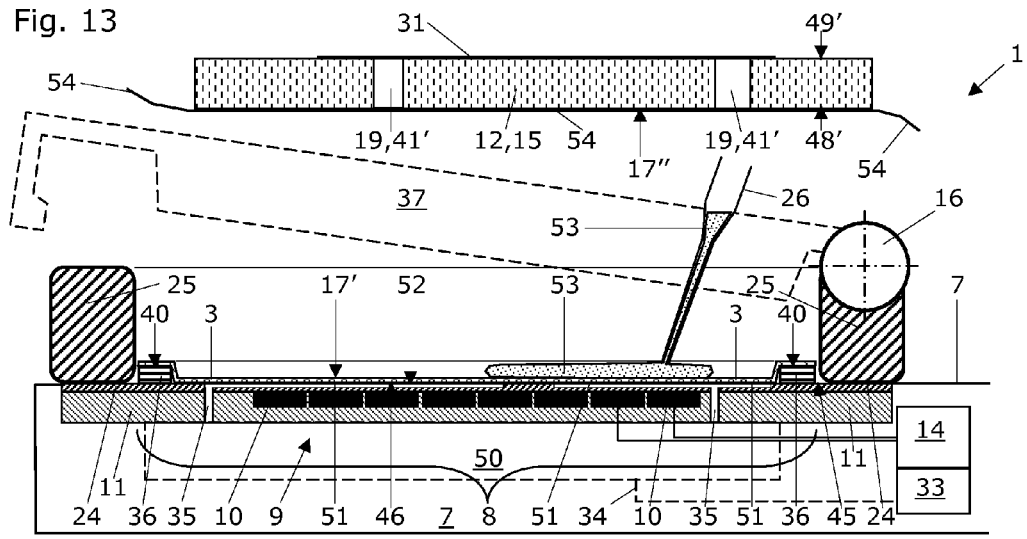
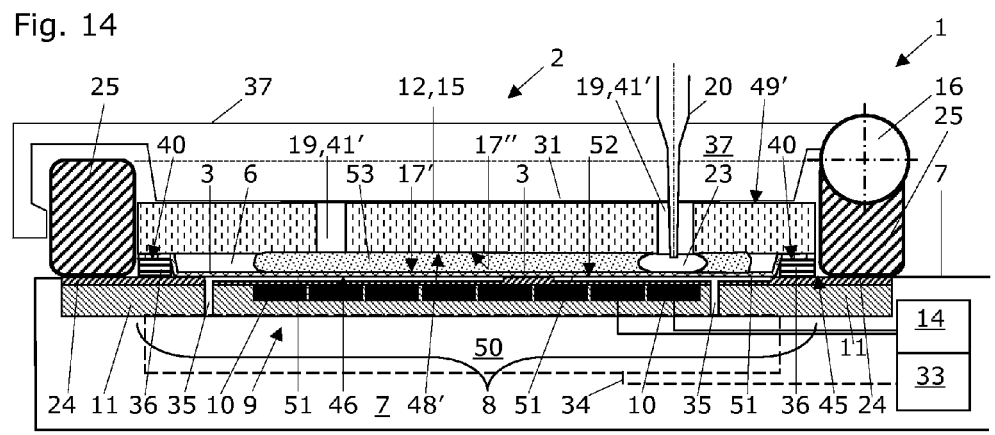
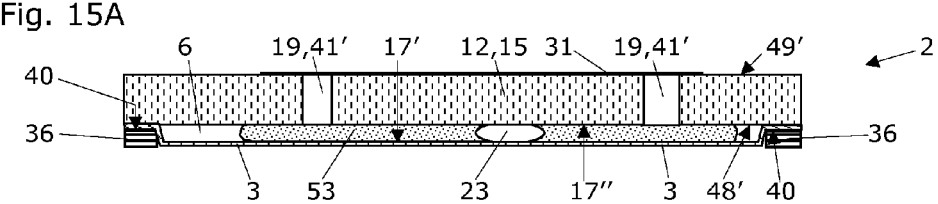
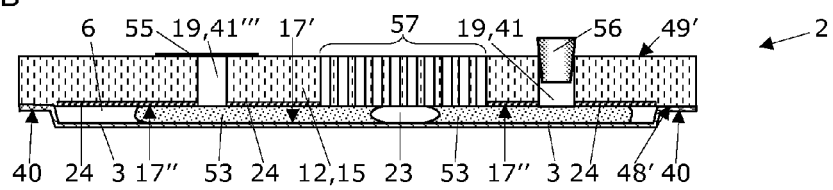

DISPOSABLE CARTRIDGE FOR MICROFLUIDICS SYSTEMS

RELATED PATENT APPLICATIONS

The present application claims priority of the international patent application PCT/EP2013/050326, filed on Sep. 1, 2013, the entire content of which being herein incorporated by explicit reference for all purposes.

FIELD OF TECHNOLOGY

The present invention relates to a disposable cartridge that can be used in or on digital microfluidics systems for manipulating samples in liquid droplets. The digital microfluidics systems comprise an electrode array supported by a substrate, and a central control unit for controlling the selection of individual electrodes of this electrode array and for providing them with individual voltage pulses for manipulating liquid droplets by electrowetting. The invention also relates to a digital microfluidics system for facilitating droplet actuated molecular techniques and to an alternative method for manipulating samples in liquid droplets digital in a microfluidics system or device.

RELATED PRIOR ART

Automated liquid handling systems are generally well known in the art. An example is the Freedom EVO® robotic workstation from the present applicant (Tecan Schweiz AG, Seestrasse 103, CH-8708 Männedorf, Switzerland). This device enables automated liquid handling in a stand-alone instrument or in automated connection with an analytical system. These automated systems typically require larger volumes of liquids (microliter to milliliter) to process. They are also larger systems that are not designed to be portable.

Many approaches to deal with the automated processing of biological samples originate from the field of microfluidics. This technical field generally relates to the control and manipulation of liquids in a small volume, usually in the micro- or nanoscale format. Liquid movement in a channel system is known per se as, e.g. being controlled by micro pumps in stationary devices or centripetal forces in rotating labware. In digital microfluidics, a defined voltage is applied to electrodes of an electrode array, so that individual droplets are addressed (electrowetting).

For a general overview of the electrowetting method, please see Washizu, IEEE Transactions on Industry Applications, Volume 34, No. 4, 1998, and Pollack et al., Lab chip, 2002, Volume 2, 96-101. Briefly, electrowetting refers to a method to move liquid droplets using arrays of microelectrodes, preferably covered by a hydrophobic layer. By applying a defined voltage to electrodes of the electrode array, a change of the surface tension of the liquid droplet, which is present on the addressed electrodes, is induced. This results in a remarkable change of the contact angle of the droplet on the addressed electrode, hence in a movement of the droplet. For such electrowetting procedures, two principle ways to arrange the electrodes are known: using one single surface with an electrode array for inducing the movement of droplets or adding a second surface that is opposite a similar electrode array and that provides at lest one ground electrode. A major advantage of the electrowetting technology is that only a small volume of liquid is required, e.g. a single droplet. Thus, liquid processing can be carried out within considerably shorter time. Furthermore the control of the liquid movement can be completely under electronic control resulting in automated processing of samples.

A device for liquid droplet manipulation by electrowetting using one single surface with an electrode array (a monoplanar arrangement of electrodes) is known from the U.S. Pat. No. 5,486,337. All electrodes are placed on a surface of a carrier substrate, lowered into the substrate, or covered by a non-wettable surface. A voltage source is connected to the electrodes. The droplet is moved by applying a voltage to subsequent electrodes, thus guiding the movement of the liquid droplet above the electrodes according to the sequence of voltage application to the electrodes.

An electrowetting device for microscale control of liquid droplet movements, using an electrode array with an opposing surface with at least one ground electrode is known from U.S. Pat. No. 6,565,727 (a biplanar arrangement of electrodes). Each surface of this device may comprise a plurality of electrodes. The drive electrodes of the electrode array are preferably arranged in an interdigitated relationship with each other by projections located at the edges of each single electrode. The two opposing arrays form a gap. The surfaces of the electrode arrays directed towards the gap are preferably covered by an electrically insulating, hydrophobic layer. The liquid droplet is positioned in the gap and moved within a non-polar filler fluid by consecutively applying a plurality of electric fields to a plurality of electrodes positioned on the opposite sites of the gap.

Containers with a polymer film for manipulating samples in liquid droplets thereon are known from WO 2010/069977 A1: A biological sample processing system comprises a container for large volume processing and a flat polymer film with a lower surface and a hydrophobic upper surface. The flat polymer film is kept at a distance to a base side of the container by protrusions. This distance defines at least one gap when the container is positioned on the film. A liquid droplet manipulation instrument comprises at least one electrode array for inducing liquid droplet movements. A substrate supporting the at least one electrode array is also disclosed as well as a control unit for the liquid droplet manipulation instrument. The container and the film are reversibly attached to the liquid droplet manipulation instrument. The system thus enables displacement of at least one liquid droplet from the at least one well through the channel of the container onto the hydrophobic upper surface of the flat polymer film and above the at least one electrode array. The liquid droplet manipulation instrument is accomplished to control a guided movement of said liquid droplet on the hydrophobic upper surface of the flat polymer film by electrowetting and to process there the biological sample.

The use of such an electrowetting device for manipulating liquid droplets in the context of the processing of biological samples is also known from the international patent application published as WO 2011/002957 A2. There, it is disclosed that a droplet actuator typically includes a bottom substrate with the control electrodes (electrowetting electrodes) insulated by a dielectric, a conductive top substrate, and a hydrophobic coating on the bottom and top substrates. Also disclosed are droplet actuator devices for replacing one or more components of a droplet actuator, i.e. disposable components that may be readily replaced (such as movable films, reversibly attachable top and bottom substrates, and self-contained replaceable cartridges).

From the international application published as WO 2011/002957 A2, droplet actuators with a fixed bottom substrate (e.g. of a PCB), with electrowetting electrodes, and with a removable or replaceable top substrate are known. A self-containing cartridge may e.g. include buffers, reagents, and filler fluid. Pouches in the cartridge may be used as fluid reservoirs and may be punctured to release fluid (e.g. a reagent or oil) into a cartridge gap. The cartridge may include a ground electrode, which may be replaced by a hydrophobic layer, and an opening for loading samples into the gap of the cartridge. Interface material (e.g. a liquid, glue or grease) may provide adhesion of the cartridge to the electrode array.

Disposable cartridges for microfluidic processing and analysis in an automated system for carrying out molecular diagnostic analysis are disclosed in WO 2006/125767 A1 (see US 2009/0298059 A1 for an English translation). The cartridge is configured as a flat chamber device (with about the size of a check card) and can be inserted into the system. A sample can be pipetted into the cartridge through a port.

Droplet actuator structures are known from the international patent application WO 2008/106678. This document particularly refers to various wiring configurations for electrode arrays of droplet actuators, and additionally discloses a two-layered embodiment of such a droplet actuator which comprises a first substrate with a reference electrode array separated by a gap from a second substrate comprising control electrodes. The two substrates are arranged in parallel, thereby forming the gap. The height of the gap may be established by spacer. A hydrophobic coating is in each case disposed on the surfaces which face the gap. The first and second substrate may take the form of a cartridge, eventually comprising the electrode array.

OBJECTS AND SUMMARY OF THE PRESENT INVENTION

It is an object of the present invention to suggest an alternative disposable cartridge for use in or on digital microfluidics systems or digital microfluidics devices which are configured to accommodate one or more such disposable cartridges for manipulating samples in liquid droplets.

This object is achieved in that a first alternative disposable cartridge is provided. The first alternative disposable cartridge of the present invention comprises:
(a) a bottom layer with a first hydrophobic surface that is impermeable to liquids and that is configured as a working film for manipulating samples in liquid droplets thereon utilizing an electrode array of a digital microfluidics system when the bottom layer of the disposable cartridge is placed over said electrode array;
(b) a plane rigid cover plate comprising a lower surface, at least one through hole located at a loading site, and a second hydrophobic surface; and
(c) a gap that is located between the first hydrophobic surface of the bottom layer and the second hydrophobic surface of the rigid cover plate.

The first alternative disposable cartridge of the present invention is characterized in that the bottom layer is configured as a flexible film that is configured to be laid on an uppermost surface of a cartridge accommodation site of the digital microfluidics system and to be attracted to and spread over said uppermost surface by the underpressure in an evacuation space, which preferably is defined by the flexible bottom layer of the disposable cartridge, an uppermost surface of the cartridge accommodation site, and a gasket of the digital microfluidics system or of the disposable cartridge.

The first alternative disposable cartridge of the present invention is further characterized in that the disposable cartridge is configured to be assembled at the cartridge accommodation site of the digital microfluidics system, the lower surface of the rigid cover plate and the flexible bottom layer being configured as sealingly attachable to each other along a circumference of the flexible bottom layer by mutual contacting the lower surface of the rigid cover plate and the circumference of the flexible bottom layer that is spread over the uppermost surface of the cartridge accommodation site of the digital microfluidics system.

The first alternative disposable cartridge of the present invention is further characterized in that the assembled disposable cartridge is configured to be removed from the cartridge accommodation site in one piece that comprises the bottom layer, the plane rigid cover plate, and the gap that potentially comprises samples and processing fluids.

Preferably, the plane rigid cover plate comprises electrically conductive material or is formed of electrically conductive material. Optionally, the second hydrophobic surface may be provided by the plane rigid cover plate or by a layer attached to the plane rigid cover plate. The second hydrophobic surface may be or may be not impermeable to liquids, it is preferred however that the second hydrophobic surface is at least permeable to ions.

This object is achieved in that a second alternative disposable cartridge is provided. The second alternative disposable cartridge of the present invention comprises:
(a) a body with a lower surface, an upper surface, and at least one through hole;
(b) a bottom layer with a first hydrophobic surface that is impermeable to liquids and that is configured as a working film for manipulating samples in liquid droplets thereon utilizing an electrode array of a digital microfluidics system when the bottom layer of the disposable cartridge is placed over said electrode array;
(c) an electrically conductive material attached to the lower surface of the body, the electrically conductive material being configured to provide the lower surface of the body with a second hydrophobic surface; and
(d) a gap that is located between the first hydrophobic surface of the bottom layer and the second hydrophobic surface of the electrically conductive material.

The second alternative disposable cartridge of the present invention is characterized in that the bottom layer is configured as a flexible film that is sealingly attached to the electrically conductive material of the disposable cartridge along a circumference of the flexible bottom layer, the disposable cartridge thus being devoid of a spacer that is located between the flexible bottom layer and the electrically conductive material for defining a particular distance between said first hydrophobic surface and said second hydrophobic surface. The second alternative disposable cartridge of the present invention is further characterized in that the at least one through hole of the body is configured as a loading site for transferring processing liquids, reagents or samples into the gap.

Optionally, the electrically conductive material that provides the second hydrophobic surface may be or may be not impermeable to liquids, it is preferred however that the electrically conductive material that provides the second hydrophobic surface is at least permeable to ions.

It is a further object of the present invention to suggest a microfluidics system or device into or onto which one or more such disposable cartridges for manipulating samples in liquid droplets therein can be placed.

This object is achieved in that an alternative digital microfluidics system is provided. The alternative digital microfluidics system for manipulating samples in liquid droplets within the gap between a first hydrophobic surface of a bottom layer and a second hydrophobic surface of at least one disposable cartridge of the present invention comprises:
(a) a base unit with at least one cartridge accommodation site that is configured for taking up one disposable cartridge;
(b) an electrode array located at said at least one cartridge accommodation site of the base unit, the electrode array being supported by a bottom substrate and substantially extending in a first plane and comprising a number of individual electrodes;
(c) a central control unit for controlling the selection of the individual electrodes of said electrode array and for providing these electrodes with individual voltage pulses for manipulating liquid droplets within the gap of said cartridge by electrowetting,
(d) a number of suction holes that penetrate the electrode array and/or the bottom substrate and that are located at the cartridge accommodation site of the base unit;
(e) a vacuum source for establishing an underpressure in an evacuation space; and
(f) a number of vacuum lines that link the suction holes to the vacuum source.

A "number of vacuum lines" can be interpreted as one or more vacuum lines.

The alternative digital microfluidics system of the present invention is characterized in that a gasket of the digital microfluidics system or of a disposable cartridge is configured to seal at said cartridge accommodation site the evacuation space, which is defined by a flexible bottom layer of a disposable cartridge, an uppermost surface of the cartridge accommodation site, and the gasket.

The digital microfluidics system of the present invention is further characterized in that the underpressure in the evacuation space causes the flexible bottom layer that is placed at the cartridge accommodation site to be attracted to and spread over the uppermost surface of the cartridge accommodation site of the digital microfluidics system, the gasket defining a particular distance between said first hydrophobic surface and said second hydrophobic surface.

Preferably, the gasket is of a flexible material that is stiff enough to undergo only a minimal compression and thus combining the task of sealing the evacuation space and of defining the final gap height. Preferred materials for this gasket are e.g. rings of natural rubber or a DuPont performance elastomer such as Viton®, a fluorocarbon rubber or Neoprene®, a polychloroprene rubber. The preferred embodiment of the gasket of the first alternative digital microfluidics system is an X-ring or square ring, a square ring being the most preferred.

It is yet a further object of the present invention to suggest an alternative method for manipulating samples in liquid droplets using a digital microfluidics system or device.

This further object is achieved in that an alternative method for manipulating samples in liquid droplets that adhere to a hydrophobic surface of a working film in a digital microfluidics system or device is proposed. The alternative method according to the present invention comprises the steps of:
(a) providing a working film in the form of a bottom layer with a first hydrophobic surface;
(b) providing a digital microfluidics system with an electrode array that substantially extends in a first plane and that comprises a number of individual electrodes supported by a bottom substrate and connected to a central control unit of the digital microfluidics system for controlling the selection of individual electrodes of said electrode array and for providing these electrodes with individual voltage pulses for manipulating said liquid droplets on said first hydrophobic surface by electrowetting; and
(c) providing a gasket for defining a gap between a second hydrophobic surface of a cartridge and said first hydrophobic surface of the bottom layer.

The alternative method for manipulating samples in liquid droplets of the present invention is characterized in that the method further comprises the steps of:
(d) placing the bottom layer that is configured as a flexible film on an uppermost surface of a cartridge accommodation site of the digital microfluidics system and thereby creating an evacuation space which is defined by said uppermost surface, the gasket that also is provided at the cartridge accommodation site, and the flexible bottom layer;
(e) establishing an underpressure in said evacuation space using a vacuum source that is linked to a number of suction holes which penetrate the electrode array and/or the bottom substrate and which are located at the cartridge accommodation site of a base unit of the digital microfluidics system, the gasket sealing the evacuation space and the underpressure in the evacuation space causing the flexible bottom layer to be attracted to and spread over the uppermost surface of the cartridge accommodation site of the digital microfluidics system;
(f) adding processing liquids to said first hydrophobic surface of the flexible bottom layer;
(g) placing a rigid cover plate with a lower surface on the flexible bottom layer, contacting said lower surface to and sealingly attaching said lower surface with a circumference of the flexible bottom layer, thereby assembling a disposable cartridge at the cartridge accommodation site of the digital microfluidics system, the gasket defining a particular distance between said first hydrophobic surface and said second hydrophobic surface; and
(h) adding at least one sample droplet to the gap and manipulating said sample droplet by electrowetting.

Additional and inventive features and preferred embodiments and variants of the digital microfluidics system, the disposable cartridge, and the method for manipulating samples in liquid droplets derive from the respective dependent claims.

Advantages of the present invention comprise:
A gasket between the flexible bottom layer and the uppermost surface of the cartridge accommodation site of the digital microfluidics system together with the geometry of the rigid cover, the flexible bottom layer and an underpressure applied to the underside of this flexible bottom layer is sufficient to define the gap between the hydrophobic surface of the flexible bottom layer and the lower surface of the rigid cover that enclose the gap Alternatively, a gasket between the cartridge and the PCB of the digital microfluidics system together with the geometry of the cartridge, the flexible bottom layer and an underpressure applied to the underside of this flexible bottom layer is sufficient to define the gap between the two films that enclose the gap.

The disposable cartridge of the present invention does not need a spacer between the hydrophobic surface of the flexible bottom layer and the lower surface of the rigid cover that enclose the gap where the electrowetting takes place.

Alternatively, the disposable cartridge of the present invention does not need a spacer between the two films that enclose the gap where the electrowetting takes place.

The gasket can be a part of the flexible bottom layer or can be fixed to the uppermost surface of the PCB or cartridge accommodation site.

The gasket can be a part of the disposable cartridge or can be fixed to the uppermost surface of the PCB or cartridge accommodation site.

In any case the disposable cartridge, whether it is prefabricated or assembled at the cartridge accommodation site of the digital microfluidics system, can be withdrawn from the cartridge accommodation site and further processed or discarded without any danger of contaminating the surroundings or operating personal.

BRIEF INTRODUCTION OF THE DRAWINGS

Figure 2:
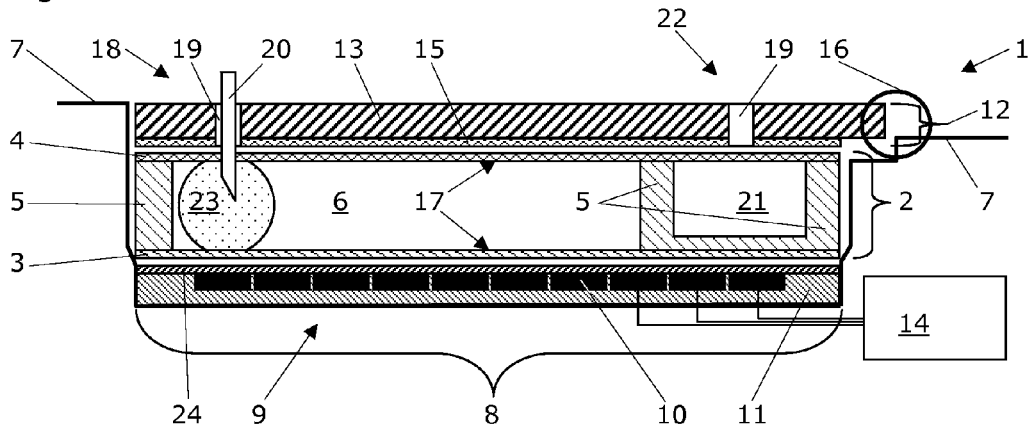
Figure 3:
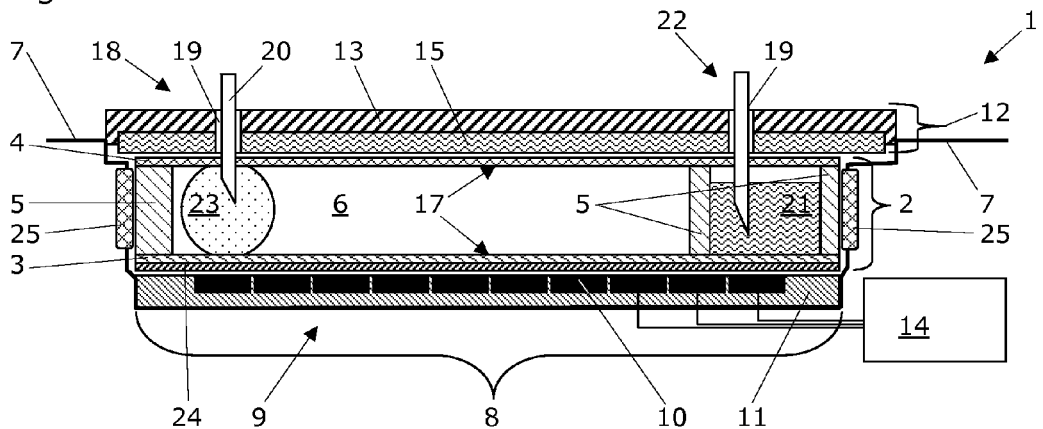
Figure 4:
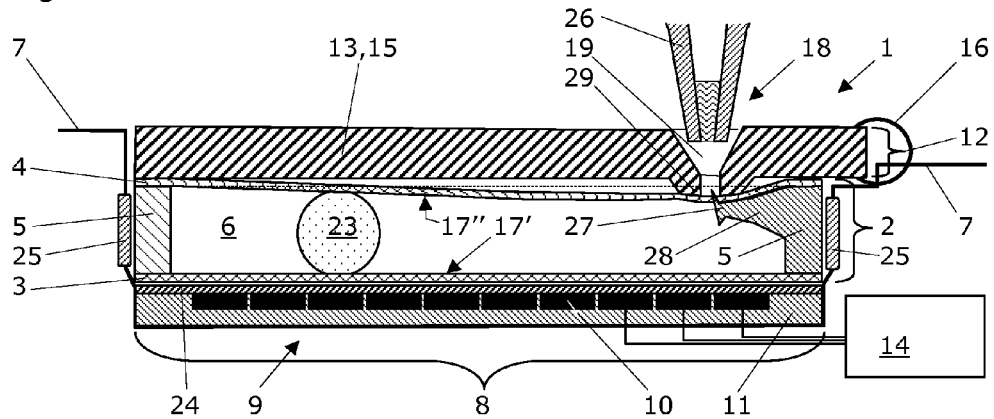
Figure 5:
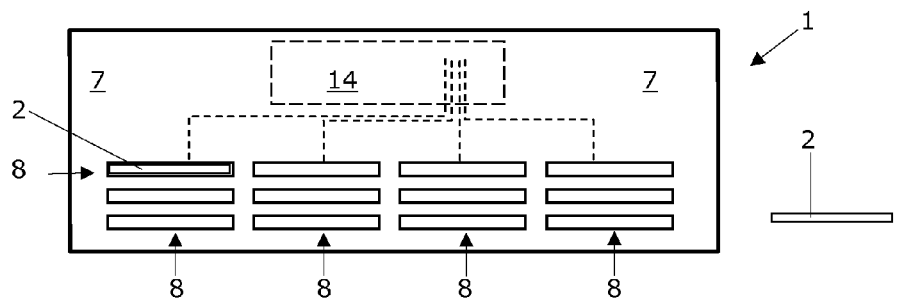
Figure 6A:
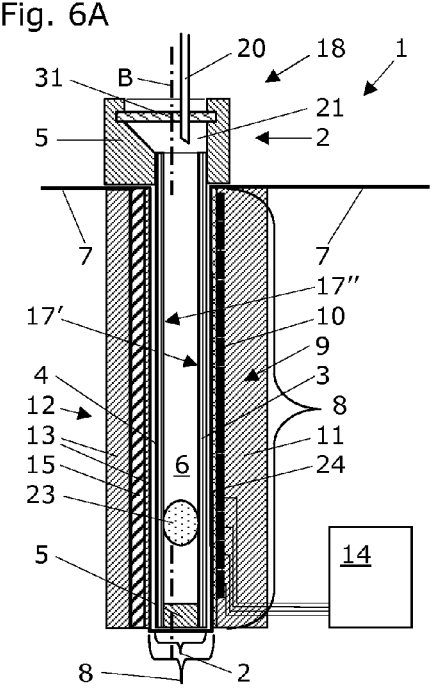
Figure 6B:
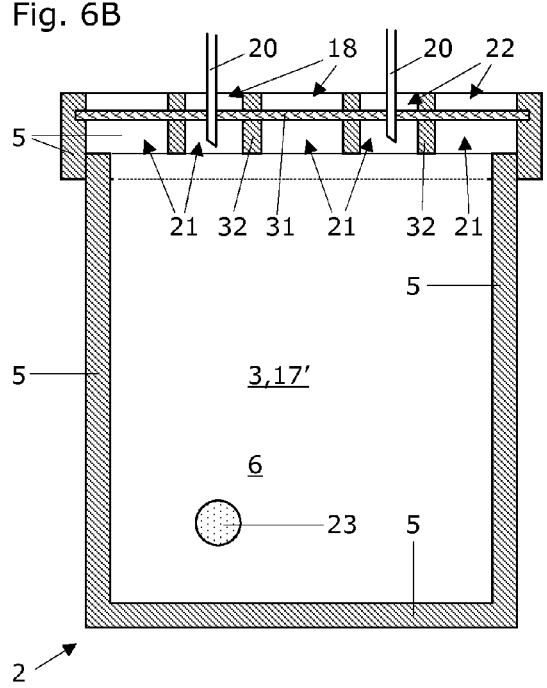
Figure 7:
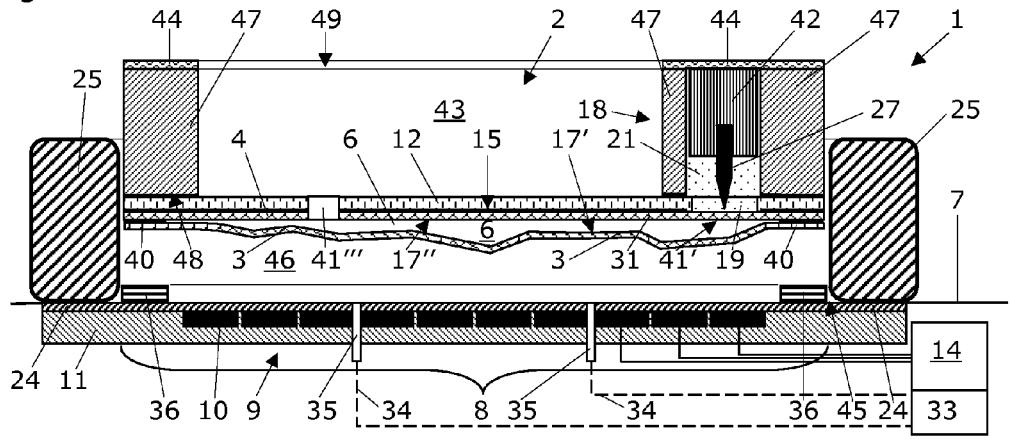
Figure 8:
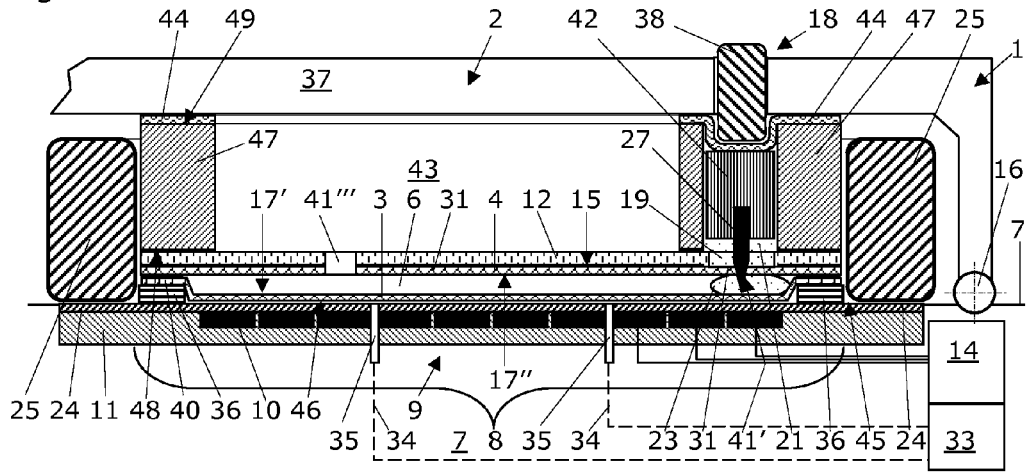
Figure 9:
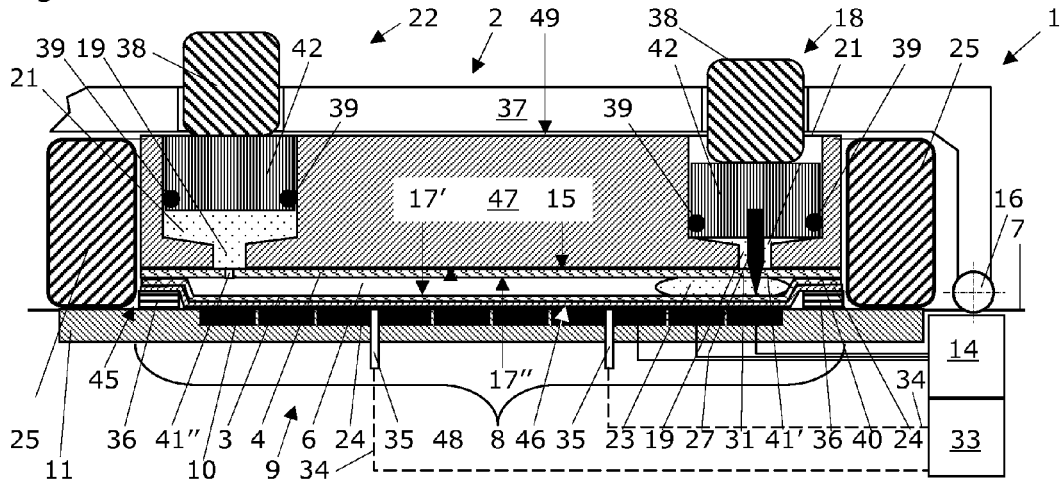
Figure 10:
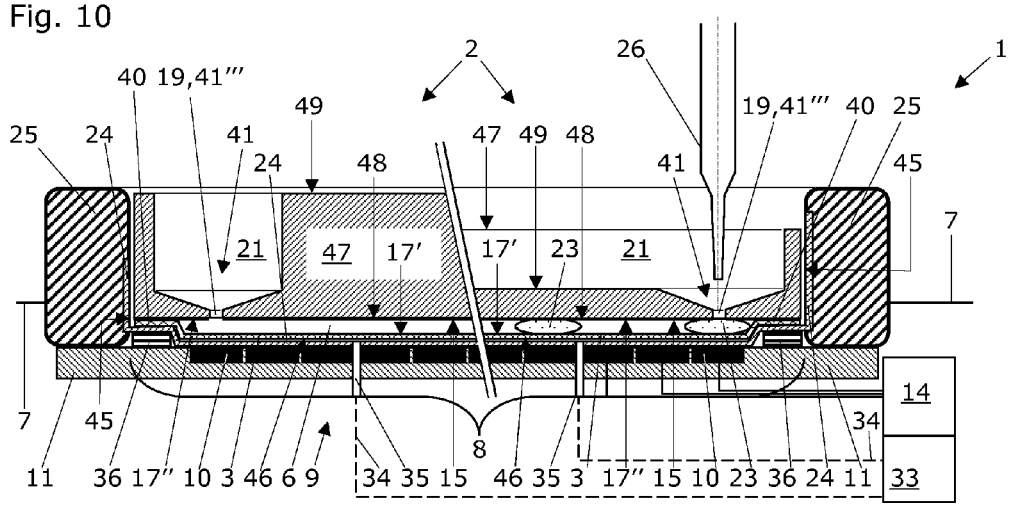
Figure 11A:
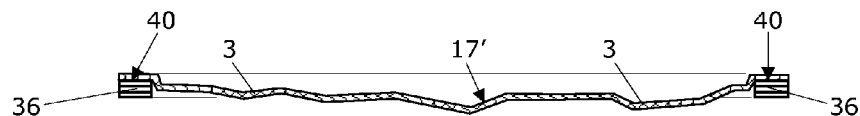
Figure 11B:
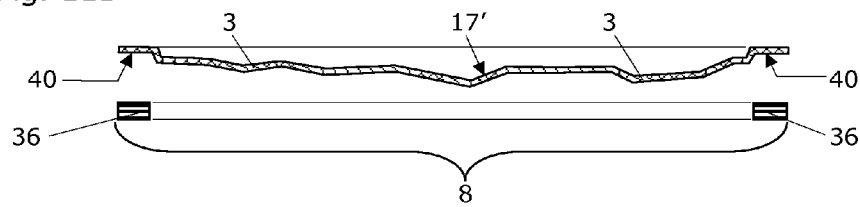
Figure 12:
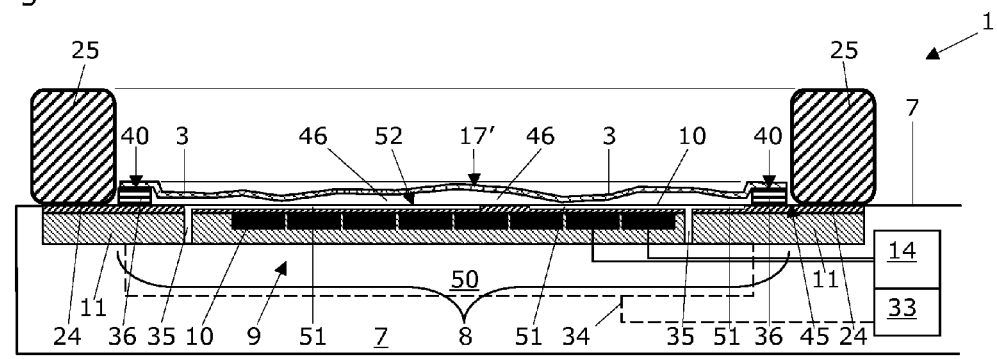

The self-contained disposable cartridge, the digital microfluidics system, and the method for manipulating samples according to the present invention are explained with the help of the attached schematic drawings that show selected and exemplary embodiments of the present invention without narrowing the scope and gist of this invention. It is shown in:

FIG. 1 an overview over a digital microfluidics system that is equipped with a central control unit and a base unit, with four cartridge accommodation sites that each comprise an electrode array, and a movable cover plate;

FIG. 2 a section view of one cartridge accommodation site with a disposable cartridge according to a first embodiment accommodated therein;

FIG. 3 a section view of one cartridge accommodation site with a disposable cartridge according to a second embodiment accommodated therein;

FIG. 4 a section view of one cartridge accommodation site with a disposable cartridge according to a third embodiment accommodated therein;

FIG. 5 an overview over a digital microfluidics system that is equipped with a central control unit and a base unit, with twelve cartridge accommodation sites that each comprise an electrode array and a fixed cover plate;

FIG. 6 section views of one cartridge accommodation site with a disposable cartridge according to a fourth embodiment accommodated therein, wherein:

FIG. 6A shows a top-entry cartridge inserted into a substantially vertical cartridge accommodation site with a substantially vertical electrode array and cover plate, and FIG. 6B shows the top-entry cartridge as viewed from the section plane B indicated in FIG. 6A;

FIG. 7 a section view of one disposable cartridge before reaching its accommodation site, the disposable cartridge being configured according to a fifth embodiment;

FIG. 8 a section view of the disposable cartridge of FIG. 7 after reaching its accommodation site, the disposable cartridge being configured according to a fifth embodiment and being hold in place by a clamp;

FIG. 9 a section view of a disposable cartridge after reaching its accommodation site, the disposable cartridge being configured according to an sixth embodiment and being hold in place by a clamp;

FIG. 10 a section view of a disposable cartridge after reaching its accommodation site, the disposable cartridge being configured according to a seventh embodiment and being hold in place without a clamp;

FIG. 11A a section view of a flexible bottom layer with attached gasket, this bottom layer-gasket combination being insertable at a cartridge accommodation site of a digital microfluidics system;

FIG. 11B a section view of a flexible bottom layer without gasket attached, the gasket being a part of the cartridge accommodation site of the digital microfluidics system, this bottom layer being insertable at a cartridge accommodation site of a digital microfluidics system;

FIG. 12 a section view of a flexible bottom layer with or without gasket attached, positioned and defining an evacuation space at the cartridge accommodation site of the digital microfluidics system;

FIG. 13 a section view of a flexible bottom layer with or without gasket attached, attracted and spread over the uppermost surface of the cartridge accommodation site of the digital microfluidics system during optional providing of oil onto the flexible bottom layer;

FIG. 14 a section view of a disposable cartridge as assembled at the cartridge accommodation site of the digital microfluidics system, the plane rigid cover plate of the cartridge being pressed to the flexible bottom layer with the assistance of a clamp;

FIG. 15A a section view of a used disposable cartridge after removal from the cartridge accommodation site of the digital microfluidics system, the gasket being a part of the cartridge;

FIG. 15B a section view of a used disposable cartridge after removal from the cartridge accommodation site of the digital microfluidics system, the gasket being a part of the digital microfluidics system.

DETAILED DESCRIPTION OF THE PRESENT INVENTION

The FIG. 1 shows an overview over an exemplary digital microfluidics system 1 that is equipped with a central control unit 14 and a base unit 7, with four cartridge accommodation sites 8 that each comprise an electrode array 9, and a cover plate 12. The digital microfluidics system 1 is configured for manipulating samples in liquid droplets 23 within disposable cartridges 2 that contain a bottom layer 3, a top layer 4, and eventually a spacer 5 that defines a gap 6 between the bottom and top layers 3,4. Accordingly, the samples in liquid droplets 23 are manipulated in the gap 6 of the disposable cartridge 2.

A typical digital microfluidics system 1 comprises a base unit 7 with at least one cartridge accommodation site 8 that is configured for taking up a disposable cartridge 2. The digital microfluidics system 1 can be a stand alone and immobile unit, on which a number of operators is working with cartridges 2 that they bring along. The digital microfluidics system 1 thus may comprise a number of cartridge accommodation sites 8 and a number of electrode arrays 9, so that a number of cartridges 2 can be worked on simultaneously and/or parallel. The number of cartridge accommodation sites 8, electrode arrays 9, and cartridges 2 may be 1 or any number between e.g. 1 and 100 or even more; this number e.g. being limited by the working capacity of the central control unit 14.

It may be preferred to integrate the digital microfluidics system 1 into a liquid handling workstation or into a Freedom EVO® robotic workstation, so that a pipetting robot can be utilized to transfer liquid portions and/or sample containing liquids to and from the cartridges 2.

Alternatively, the system 1 can be can be configured as a hand held unit which only comprises and is able to work with a low number, e.g. a single disposable cartridge 2. Every person of skill will understand that intermediate solutions that are situated in-between the two extremes just mentioned will also operate and work.

A typical digital microfluidics system 1 also comprises at least one electrode array 9 that substantially extends in a first plane and that comprises a number of individual electrodes 10. Such an electrode array 9 is located at each one of said cartridge accommodation sites 8 of the base unit 7. Preferably each electrode array 9 is supported by a bottom substrate 11, which bottom substrate 11 is fixed to the base unit 7. It is noted that the expressions "electrode array" and "electrode layout" or the expressions "bottom substrate" and "printed circuit board (PCB)" are utilized herein as synonyms in each case and that a PCB may comprise a bottom substrate 11 and an electrode array 9.

A typical digital microfluidics system 1 also comprises at least one cover plate 12 with a top substrate 13. In each case, at least one cover plate 12 is located at said cartridge accommodation sites 8. The top substrate 13 of the cover plate 12 and the bottom substrate 11 or PCB with the electrode array 9 define a space or cartridge accommodation site 8 respectively. In a first variant (see the two cartridge accommodation sites 8 in the middle of the base unit 7), the cartridge accommodation sites 8 are configured for receiving a slidingly inserted disposable cartridge 2 that is movable in a direction substantially parallel with respect to the electrode array 9 of the respective cartridge accommodating site 8. Such front- or top-loading can be supported by a drawing-in automatism that, following a partial insertion of a disposable cartridge 2, transports the cartridge 2 to its final destination within the cartridge accommodation site 8, where the cartridge 2 is precisely seated. Preferably, these cartridge accommodation sites 8 do not comprise a movable cover plate 12. After carrying out all intended manipulations to the samples in liquid droplets, the used cartridges 2 can be ejected by the drawing-in automatism and transported to an analysis station or discarded.

In a second variant (see the two cartridge accommodation sites 8 on the right and left of the base unit 7), the cartridge accommodation sites 8 comprise a cover plate 12 that is configured to be movable with respect to the electrode array 9 of the respective cartridge accommodating site 8. The cover plate 12 preferably is configured to be movable about one or more hinges 16 and/or in a direction that is substantially normal to the electrode array 9.

A typical digital microfluidics system 1 also comprises a central control unit 14 for controlling the selection of the individual electrodes 10 of said at least one electrode array 9 and for providing these electrodes 10 with individual voltage pulses for manipulating liquid droplets within said cartridges 2 by electrowetting. As partly indicated in FIG. 1, every single individual electrode 10 is operatively connected to the central control unit 14 and therefore can be independently addressed by this central control unit 14, which also comprises the appropriate sources for creating and providing the necessary electrical potentials in a way known in the art.

The at least one cover plate 12 further comprises an electrically conductive material 15 that extends in a second plane and substantially parallel to the electrode array 9 of the cartridge accommodation site 8 the at least one cover plate 12 is assigned to. This electrically conductive material 15 of the cover plate 12 preferably is configured to be connected to a source of an electrical ground potential. This conductive material 15 contributes to the electrowetting movements of the liquid droplets manipulated in the digital microfluidics system 1.

The applicants surprisingly found that the conductive material 15 also contributes to the electrowetting movements of the liquid droplets manipulated in the digital microfluidics system 1, if there is no connection between the conductive material 15 of the cover plate 12 and any source of a certain electrical (e.g. ground) potential. Thus, the cover plate 12 can be configured to be movable in any arbitrary direction and no electrical contacts have to be taken in into consideration when selecting a particularly preferred movement of the cover plate 12. Thus, the cover plate 12 may be configured to be also movable in a direction substantially parallel to the electrode array 9 and for carrying out a linear, circular or any arbitrary movement with respect to the respective electrode array 9 of the base unit 7.

The FIG. 2 shows a section view of one exemplary cartridge accommodation site 8 with a disposable cartridge 2 according to a first embodiment accommodated therein. The cover plate 12 is mechanically connected with the base unit 7 of the digital microfluidics system 1 via a hinge 16; thus, the cover plate 12 can swing open and a disposable cartridge 2 can be placed on the cartridge accommodation site 8 via top-entry loading (see FIG. 1). The electrically conductive material 15 of the cover plate 12 is configured as a thin metal plate or metal foil that is attached to the top substrate 13.

Alternatively, the electrically conductive material 15 of the cover plate 12 is configured as a metal layer that is deposited onto the top substrate 13. Such deposition of the conductive material 15 may be carried out by chemical or physical vapor deposition techniques as they are known per se.

The cover plate 12 is configured to apply a force to a disposable cartridge 2 that is accommodated at the cartridge accommodation site 8 of the base unit 7. This force urges the disposable cartridge 2 against the electrode array 9 in order to position the bottom layer 3 of the cartridge as close as possible to the uppermost surface of the electrode array 9. This force also urges the disposable cartridge 2 into the perfect position on the electrode array 9 with respect to a piercing facility 18 of the cover plate 12. This piercing facility 18 is configured for introducing sample droplets into the gap 6 of the cartridge 2. The piercing facility 18 is configured as a through hole 19 that leads across the entire cover plate 12 and that enables a piercing pipette tip 20 to be pushed through and pierce the top layer 4 of the cartridge 2. The piercing pipette tip 20 may be a part of a handheld pipette (not shown) or of a pipetting robot (not shown).

In this case, the electrode array 9 is covered by a dielectric layer 24. The electrode array 9 is fixed to a bottom substrate 11 and every individual electrode 10 is electrically and operationally connected with the central control unit 14 (only three connections of the ten electrodes 10 are drawn here). The digital microfluidics system 1 is configured for manipulating samples in liquid droplets 23 within disposable cartridges 2 that contain a gap 6. Accordingly, the samples in liquid droplets 23 are manipulated in the gap 6 of the disposable cartridge 2.

The disposable cartridge 2 comprises a bottom layer 3, a top layer 4, and a spacer 5 that defines a gap 6 between the bottom and top layers 3,4 for manipulating samples in liquid droplets 23 in this gap 6. The bottom layer 3 and the top layer 4 comprise a hydrophobic surface 17 that is exposed to the gap 6 of the cartridge 2. The bottom layer 3 and the top layer 4 of the cartridge 2 are entirely hydrophobic films or at least comprise a hydrophobic surface that is exposed to the gap 6 of the cartridge 2. It is clear from this FIG. 2, that the cartridge 2 does not have a conductive layer. The spacer 5 of the cartridge 2 here at least partially is configured as a body that includes compartments 21 for reagents needed in an assay that is applied to the sample droplets in the gap 6.

The FIG. 3 shows a section view of one exemplary cartridge accommodation site 8 with a disposable cartridge 2 according to a second embodiment accommodated therein. Different to the previous embodiment, the cover plate 12 is mechanically connected with the base unit 7 of the digital microfluidics system 1 and immovably fixed therewith. The electrically conductive material 15 of the cover plate 12 is configured as a thick metal plate that is attached to the top substrate 13. Here, the cover plate 12 is not configured to apply a force to the disposable cartridge 2 that is accommodated at the cartridge accommodation site 8 of the base unit 7; thus, the cover plate 12 stays in place and a disposable cartridge 2 can be placed on the cartridge accommodation site 8 via front-entry loading. Such front-entry loading usually includes a movement of the disposable cartridge 2 in a direction that is parallel to the electrode array 9 (see FIG. 1). In order to enable proper drawing-in of the disposable cartridge 2 and to neatly position the cartridge at the accommodation site 8, the base unit 7 preferably is equipped with insertion guides 25. These insertion guides 25 preferably are from a self-lubricating plastic material, such as tetrafluorethylene and preferably leave a space between them that is just sufficient for slidingly inserting the disposable cartridge 2. Alternatively the electrically conductive material 15 of the cover plate 12 is configured as a metal plate, a metal foil, or a metal layer that is sandwiched between materials of the top substrate 13 (see FIG. 8A).

The disposable cartridge 2 of FIG. 3 comprises a bottom layer 3, a top layer 4, and a spacer 5 that defines a gap 6 between the bottom and top layers 3,4 for manipulating samples in liquid droplets 23 in this gap 6. The bottom layer 3 and the top layer 4 comprise a hydrophobic surface 17 that is exposed to the gap 6 of the cartridge 2. The bottom layer 3 and the top layer 4 of the cartridge 2 are entirely hydrophobic films or at least comprise a hydrophobic surface that is exposed to the gap 6 of the cartridge 2. As a difference to the one depicted in FIG. 2, this cartridge 2 has a dielectric layer 24 that is attached to or forms a part of the bottom layer 3. Thus, the bottom layer 3 is covered by a dielectric layer 24 or the bottom layer 3 itself is made from a dielectric material. In consequence, the electrode array 9 does not need to have such a dielectric layer 24. The spacer 5 of the cartridge 2 here at least partially is configured as a body that includes compartments 21 for reagents needed in an assay that is applied to the sample droplets in the gap 6. In this case, the electrode array 9 is not covered by a dielectric layer 24.

The electrode array 9 is fixed to a bottom substrate 11 and every individual electrode 10 is electrically and operationally connected with the central control unit 14 (only three connections of the ten electrodes 10 are drawn here). The digital microfluidics system 1 is configured for manipulating samples in liquid droplets 23 within disposable cartridges 2 that contain a gap 6. Accordingly, the samples in liquid droplets 23 are manipulated in the gap 6 of the disposable cartridge 2.

The cover plate 12 also includes a piercing facility 18 that is configured for introducing sample droplets into the gap 6 of the cartridge 2. The piercing facility 18 is configured as a through hole 19 that leads across the entire cover plate 12 and that enables a piercing pipette tip 20 to be pushed through and pierce the top layer 4 of the cartridge 2. The piercing pipette tip 20 may be a part of a handheld pipette (not shown) or of a pipetting robot (not shown). The cover plate 12 here comprises additional piercing facilities 22 for a piercing pipette tip 20 to be pushed through a through hole 19 that penetrates the cover plate 12, to pierce the top layer 4 of the cartridge 2 and to withdraw reagent portions from the compartments 21 and for introducing said reagent portions into the gap 6 of the cartridge 2. Here, the compartment 21 is configured as a cutout in the body of the spacer 5, the cutout being closed by the bottom layer 3 and top layer 4.

The FIG. 4 shows a section view of one exemplary cartridge accommodation site 8 with a disposable cartridge 2 according to a third embodiment accommodated therein. The cover plate 12 is mechanically connected with the base unit 7 of the digital microfluidics system 1 by a hinge 16. In order to enable proper top-loading of the disposable cartridge 2 and to neatly position the cartridge at the accommodation site 8, the base unit 7 preferably is equipped with insertion guides 25. These insertion guides 25 preferably are from a self-lubricating plastic material, such as tetrafluorethylene (PTFE) and preferably leave a space between them that is just sufficient for slidingly inserting the disposable cartridge 2. As a first alternative solution, the electrically conductive material 15 of the cover plate 12 is made of metallic conductive material and comprises both the top substrate 13 and the electrically conductive material 15 as a single integrated part. Alternatively, the electrically conductive material 15 of the cover plate 12 is configured as compound, such as titanium indium oxide (TIO) or a plastic material with electrically conductive filler materials that is attached or integrated into the top substrate 13 (not shown). In both cases, it may be preferred that the electrically conductive material 15 is covered by a plastic layer (not shown); the material of this plastic layer preferably being selected from a group comprising polypropylene and polyamide.

The cover plate 12 is configured to apply a force to a disposable cartridge 2 that is accommodated at the cartridge accommodation site 8 of the base unit 7. This force urges the disposable cartridge 2 against the electrode array 9 in order to position the bottom layer 3 of the cartridge as close as possible to the uppermost surface of the electrode array 9. This force also urges the disposable cartridge 2 into a defined position on the electrode array 9. In addition, a piercing facility 18 is provided: The disposable cartridge 2 according to this third embodiment comprises a piercing pin 27 that is located in the gap 6 of the cartridge 2 and that is configured for piercing the top layer 4 when the top layer 4 is displaced in a direction against the bottom layer 3. Preferably, the piercing pin 27 is attached to a pin plate 28, which pin plate 28 is connecting the piercing pin 27 with a part of the spacer 5 of the disposable cartridge 2. The cover plate 12 further comprises a through hole 19 that leads across the entire cover plate 12 and that is located in register with the piercing pin 27 of a properly positioned disposable cartridge 2 seated at the cartridge accommodation site 8. The cover plate 12 further comprises a displacement portion 29, which protrudes from the cover plate 12 for displacing the top layer 4 in a direction against the bottom layer 3. This displacement portion 29 is configured to cooperate with the piercing pin 27 when piercing the top layer 4. Thus, by utilization of this piercing facility 18, sample droplets and/or reagent portions may be introduced into the gap 6 of the cartridge 2. A portion of the through hole 19 preferably is widened such that a disposable pipette tip 26 may be used for pipetting sample droplets and/or reagent portions to the gap 6 of the disposable cartridge 2. The disposable pipette tip 26 may be a part of a handheld pipette (not shown) or of a pipetting robot (not shown).

In this case, the electrode array 9 is covered by a dielectric layer 24. The electrode array 9 is fixed to a bottom substrate 11 and every individual electrode 10 is electrically and operationally connected with the central control unit 14 (only three connections of the ten electrodes 10 are drawn here). The digital microfluidics system 1 is configured for manipulating samples in liquid droplets 23 within disposable cartridges 2 that contain a gap 6. Accordingly, the samples in liquid droplets 23 are manipulated in the gap 6 of the disposable cartridge 2.

Like in the already introduced first and second embodiments, the disposable cartridge 2 comprises a bottom layer 3, a top layer 4, and a spacer 5 that defines a gap 6 between the bottom and top layers 3,4 for manipulating samples in liquid droplets 23 in this gap 6. The bottom layer 3 and the top layer 4 comprise a hydrophobic surface 17 that is exposed to the gap 6 of the cartridge 2. The $1^{st}$ hydrophobic surface 17' is located on the inside of the bottom layer 3, and the $2^{nd}$ hydrophobic surface 17" is located on the inside of the top layer 4. The bottom layer 3 and the top layer 4 of the cartridge 2 are entirely hydrophobic films or at least comprise a hydrophobic surface that is exposed to the gap 6 of the cartridge 2. It is clear from this FIG. 4, that the cartridge 2 does not have a conductive layer. The spacer 5 of the cartridge 2 here does not deed to be configured as a body that includes compartments 21 for reagents needed in an assay that is applied to the sample droplets in the gap 6, because these reagents could be added to the gap 6 by conventional pipetting with a handheld pipette or with a pipetting robot (see above).

The piercing pin 27 of the third embodiment of the disposable cartridge 2 (see FIG. 4) is placed close to the spacer 5 with which it is connected by a self-supporting pin plate 28. Thus, the spacer 6 provides stability to the piercing pin 27 when the top layer 4 is displaced by the displacement portion 29 of the cover plate 12. Advantageously, the electrode array 9 is not involved or affected by the piercing process and all of the individual electrodes 10 can be used for electrowetting. It is preferred to add a so-called weather groove to the lower part of the piecing pin 27 (see FIG. 6) if draining the pipetted liquid down to the $1^{st}$ hydrophobic surface 17' along the self-supporting pin plate 28 should be avoided. If such draining down however is preferred, adding of such a weather groove can be omitted.

The FIG. 5 shows an overview over a digital microfluidics system 1 that is equipped with a central control unit 14 and a base unit 7, with twelve cartridge accommodation sites 8 that each comprises an electrode array 9 and a fixed cover plate 12. This base unit 7 is particularly suited for taking up cartridges 2 according to a fourth embodiment and loading these cartridges into substantially vertical cartridge accommodation sites 8 with a substantially vertical electrode array 9 and cover plate 12 (see FIG. 6). Such loading preferably is carried out by a robotized gripping device of a liquid handling workstation (not shown).

The FIG. 6 shows section views of one exemplary cartridge accommodation site 8 of a base unit 7 of digital microfluidics system 1 with a disposable cartridge 2 according to a fourth embodiment accommodated therein. It is immediately clear from the FIG. 6A, that a top-entry cartridge 2 is inserted into a substantially vertical cartridge accommodation site 8 with a substantially vertical electrode array 9 and cover plate 12. This disposable cartridge 2 comprises a bottom layer 3 and a top layer 4, and a spacer 5 that defines a gap 6 between the bottom and top layers 3,4 for manipulating samples in liquid droplets 23 in this gap 6. The bottom layer 3 and the top layer 4 comprise a hydrophobic surface 17',17" that is exposed to the gap 6 of the cartridge 2. The bottom layer 3 and the top layer 4 of the cartridge 2 are entirely hydrophobic films or at least comprise a hydrophobic surface that is exposed to the gap 6 of the cartridge 2. Like the one depicted in FIG. 2, this cartridge 2 has no dielectric layer attached to or forms a part of the bottom layer 3. In consequence, the electrode array 9 does need to have such a dielectric layer 24. This cartridge 2 preferably is filled with silicon oil.

The electrode array 9 is fixed to a bottom substrate 11 and every individual electrode 10 is electrically and operationally connected with the central control unit 14 (only four connections of the fourteen electrodes 10 are drawn here). The digital microfluidics system 1 is configured for manipulating samples in liquid droplets 23 within disposable cartridges 2 that contain a gap 6. Accordingly, the samples in liquid droplets 23 are manipulated in the gap 6 of the disposable cartridge 2.

The cover plate 12 is mechanically connected with or entirely integrated into the base unit 7 of the digital microfluidics system 1 and is not movable. Thus, a disposable cartridge 2 can be inserted into the cartridge accommodation site 8 via top-entry loading (see FIG. 5). Here, the electrically conductive material 15 of the cover plate 12 is made of metallic conductive material and is sandwiched between material of the top substrate 13. Alternatively, the electrically conductive material 15 of the cover plate 12 may be covered by a plastic layer instead or additional to the material of the top substrate 13 (not shown).

The spacer 5 also includes a piercing facility 18 that is configured for introducing sample droplets into the gap 6 of the cartridge 2. The piercing facility 18 is configured as an enlarged portion of the spacer 5. This enlarged spacer portion preferably is equipped with a pierceable, self-sealing membrane 31 that enables a piercing pipette tip 20 to be pushed through. The piercing pipette tip 20 may be a part of a handheld pipette (not shown) or of a pipetting robot (not shown). Automated delivery of liquids to or withdrawal of liquids from the gap 6 of the cartridge 2 is simplified by the relatively large piercing area provided by this enlarged spacer portion of the cartridge 2. Assuming a gap width of about 1-3 mm, the width of this piercing area preferably is about 5-10 mm and therefore has about the size of a well of a 96-well microplate, which easily can be reached by an automated pipettor of a liquid handling system or of a liquid handling workstation. The same time when providing space for compartments 21 (see also FIG. 6B), the enlarged spacer portion of the cartridge 2 also provides gripping surfaces for being gripped by an automated robot gripper (not shown) that is preferably utilized for handling the cartridges outside of the digital microfluidics system 1 and for inserting and withdrawal of the cartridges 2 from their accommodation sites 8. In addition, the enlarged spacer portion of the cartridge 2 provides an abutting surface that abuts the surface of the base unit 7 when the cartridge 2 is correctly accommodated in the accommodation site 8.

It is preferred that the electrode array 9 extends to the foremost position with respect to the surface of the base unit 7 in order to be able to move liquid droplets 23 from a compartment 21 to a distinct position on the printed circuit board (PCB) or electrode array 9. Also moving liquid droplets 23 in the opposite direction from a reaction site on the electrode array 9 to a compartment 21 is greatly preferred, especially in the case if a reaction product shall be analyzed outside of the digital microfluidics system 1 and also outside of the cartridge 2.

FIG. 6B shows the top-entry cartridge 2 of FIG. 6A as viewed from the section plane B indicated in FIG. 6A. The section runs through the gap 6 and between the bottom layer 3 and the top layer 4 of the self-containing, disposable cartridge 2. The section also crosses the spacer 5, of which a U-shaped part is located between the bottom and top layers 3,4 and an enlarged spacer portion is provided around the U-shaped part and the bottom and top layers 3,4. Preferably, the U-shaped part of the spacer 5 is of plastic material (preferably injection molded) and glued or fused to the bottom and top layers 3,4. It is preferred that the enlarged spacer portion also is produced by injection molding; this enables the provision of separating bars 32 that on the one hand create the compartments 21 below the pierceable membrane 31, and that on the other hand stabilize the pierceable membrane 31. Such stabilization preferably is provided by back-injection molding the separating bars 32 and the enlarged spacer portion to the pierceable membrane 31. Preferably, the enlarged spacer portion then is imposed on the U-shaped part of the spacer 5 with the bottom and top layers 3,4.

As already pointed out, the spacer 5 also includes a piercing facility 18 that is configured as an enlarged portion of the spacer 5. This enlarged spacer portion preferably is equipped with a pierceable self-sealing membrane 31 that enables a piercing pipette tip 20 to be pushed through. The piercing pipette tip 20 may be a part of a handheld pipette (not shown) or of a pipetting robot (not shown). The spacer 2 here comprises additional piercing facilities 22 for a piercing pipette tip 20 to be pushed through the self-sealing membrane 31 and to withdraw e.g. silicon oil from the gap 6 of the cartridge 2. In the cartridge 2 of this FIG. 6B, a liquid droplet 23 (e.g. a sample) was introduced by the piercing pipette tip 20 at the piercing facility 18 and then moved on the hydrophobic surface 17' of the bottom layer 3 to the actual position. Simultaneously with introducing the liquid droplet 23 into the compartment 21 and into the gap 6, a similar amount of silicon oil (or any other chemically inert liquid that will not mix with the liquid droplet 23) is withdrawn from the respective compartment 21 at the additional piercing facility 22. Alternative to such simultaneous balancing of liquids in the gap 6, removing of the expected quantity of oil or inert liquid can be carried out shortly before or after the insertion of the liquid droplet 23. The compartments 21 also may serve as reservoirs for storing more liquid than necessary for producing a movable liquid droplet 23 from this liquid; in consequence, a number of such droplets 23 may be produced from a single liquid volume once introduced into at least one of the compartments 21. It is advisable however, to set aside one compartment 21, for withdrawal of oil or inert liquid, and to set aside another compartment 21 for withdrawal of reagent products.

According to an alternative and very simple embodiment (not shown), a disposable cartridge 2 that comprises a bottom layer 3 and top layer 4 with hydrophobic surfaces 17',17" that in each case are directed to the gap 6, can be mounted on a PCB for electrowetting. Instead of utilizing a cover plate 12 that is equipped with an electrically conductive material 15, an electrically conductive film (e.g. an aluminum foil) can be attached to the outer surface of the top layer 4. It turned out that such a conductive film enables electrowetting even when this conductive film in not grounded. Instead of attaching an un-grounded conductive film to the cartridge, the top layer 4 can have a thin film coating on its outer surface; the thin film coating can be of any metal and deposited by chemical or physical evaporation techniques. This thin conductive film on the outer surface of the top layer 4 can even by of conductive paint. It is thus proposed to provide an electrically conductive material 15 that extends in a second plane and substantially parallel to the electrode array 9, said electrically conductive material 15 being situated on the top layer 4 of the cartridge 2 and being not connected to a source of a distinct electrical potential during manipulating samples in liquid droplets 23.

A method for manipulating samples in liquid droplets 23 that adhere to a hydrophobic surface 17 is characterized that the method comprising the steps of providing a first hydrophobic surface 17' on a bottom layer 3 of a disposable cartridge 2. This bottom layer 3 is located substantially parallel above an electrode array 9 of a digital microfluidics system 1. Said electrode array 9 substantially extends in a first plane and comprises a number of individual electrodes 10 that are supported by a bottom substrate 11 of a base unit 7 of the digital microfluidics system 1. Said electrode array 9 is connected to a central control unit 14 of the digital microfluidics system 1 for controlling the selection of individual electrodes 10 of said electrode array 9 and for providing these electrodes 10 with individual voltage pulses for manipulating said liquid droplets 23 on said first hydrophobic surface 17' by electrowetting.

The method also comprises the step of providing a second hydrophobic surface 17" substantially parallel to and in a distance to said first hydrophobic surface 17'. In this way, a gap 6 between the first and second hydrophobic surfaces 17',17" is formed.

The method further comprises providing a cover plate 12 with or without a top substrate 13. The cover plate 12 also comprises an electrically conductive material 15 that extends in a second plane and substantially parallel to the electrode array 9. It is especially preferred that the electrically conductive material 15 of the cover plate 12 is not connected to a source of a distinct electrical potential during manipulating samples in liquid droplets 23.

It is preferred that the bottom layer 3 and the top layer 4 of the cartridge 2 are entirely hydrophobic films or comprise a hydrophobic surface 17',17" that is exposed to the gap 6 of the cartridge 2. Following electrowetting and manipulating at least one liquid droplet 23 with the gap 6 of a disposable cartridge 2, the result of the manipulation or of the assay can be evaluated while the disposable cartridge 2 still is at the cartridge accommodation site 8, i.e. utilizing an analysis system of the digital microfluidics system 1 or of a workstation, the digital microfluidics system 1 is integrated into. Alternately, the disposable cartridges 2 can be taken out of the base unit 7 of the digital microfluidics system 1 and analyzed elsewhere.

After analysis, the disposable cartridges 2 can be disposed and the electrode array 9 can be reused. Because the components of the digital microfluidics system 1 never come into contact with any samples or reagents when working with the first or second embodiment of the cartridge 2, such re-usage with other disposable cartridges 2 can be immediately and without any intermediate cleaning. Because the through hole 19 of the cover plate 12 of the digital microfluidics system 1 may come into contact with samples and reagents when working with the third or fourth embodiment of the cartridge 2, such re-usage with other disposable cartridges 2 can be carried out after some intermediate cleaning or after replacement of the cover plates 12.

It is an aim of the present invention to provide removable and disposable cartridges with working films that separate the liquid droplets 23 from the electrode array 9 during manipulation of the liquid droplets 23 by electrowetting. As shown in the different embodiments of the self-containing disposable cartridge 2 presented in the above specification, the removable and disposable films preferably are provided as a bottom layer 3 and a top layer 4 of a cartridge 2.

In a preferred embodiment, the bottom layer 3 of the cartridge 2 is attracted to the PCB by vacuum. Small evacuation holes in the PCB are connected to a vacuum pump for this purpose. Applying such vacuum attraction to the bottom layer 3 enables avoiding the use of any liquids or adhesives for better contacting the bottom layer 3 of the cartridge 2 to the surface of the electrode array 9 or to an uppermost surface of the cartridge accommodation site 8 respectively.

In the attached FIGS. 7, 8, 9, and 10, especially preferred embodiments of a disposable cartridge according to a fifth and sixth embodiment are shown. In each case, the disposable cartridge 2 comprises a body 47 with at least one compartment 21 that is configured to hold therein processing liquids, reagents or samples. At least one of said compartments 21 comprises a through hole 19 for delivering at least some of its content to a gap 6 below. The disposable cartridge 2 also comprises a bottom layer 3 with a first hydrophobic surface 17' that is impermeable to liquids and that is configured as a working film for manipulating samples in liquid droplets 23 thereon utilizing an electrode array 9 of a digital microfluidics system 1 when the bottom layer 3 of the disposable cartridge 2 is placed over said electrode array 9. The disposable cartridge 2 further comprises a top layer 4 with a second hydrophobic surface 17" that is at least permeable to ions and that is attached to a lower surface 48 of the body 47 of the disposable cartridge 2. Moreover, the disposable cartridge 2 comprises a gap 6 that is located between the first hydrophobic surface 17' of the bottom layer 3 and the second hydrophobic surface 17" of the top layer 4. The bottom layer 3 of the inventive cartridge 2 is configured as a flexible film that is sealingly attached to the top layer 4 along a circumference 40 of the flexible bottom layer 3. Thus, the disposable cartridge 2 is devoid of any spacer 5 that is located between the flexible bottom layer 3 and the top layer 4 for defining a particular distance between said first hydrophobic surface 17' and said second hydrophobic surface 17". The top layer 4 is configured to provide a seal between a lower end of at least one compartment 21 and the gap 6. In addition, the top layer 4 comprises loading sites 41 for transferring processing liquids, reagents or samples into the gap 6.

In FIG. 7, a section view of one disposable cartridge 2 before reaching its accommodation site 8 is presented. The flexible bottom layer 3 is seen as it is only attached to the top layer 4 around its circumference 40, the majority of the bottom layer 3 being loosely suspended from its circumference 40 and being not in contact with the top layer 4. Accordingly, before correctly placing the disposable cartridge 2 in or on the cartridge accommodation site 8, the gap 6 is enclosed but not defined in its width and parallel orientation. The body 47 of the disposable cartridge 2 here comprises an essentially flat lower surface 48 and is configured as a frame structure with a central opening 43 that penetrates the entire frame structure.

In FIG. 8, a section view of the disposable cartridge 2 of FIG. 7 is depicted after the disposable cartridge 2 reaching its cartridge accommodation site 8 on the electrode array of a digital microfluidics system 1. The disposable cartridge 2 is configured according to the fifth embodiment and is hold in place by a clamp 37. On one side, the clamp 37 preferably is attached to the substrate 11 of the base unit 7 of the digital microfluidics system 1 by a hinge 16. On the other side, the clamp 37 may be attached to the substrate 11 of the base unit 7 of the digital microfluidics system 1 by e.g. a clip, a snap-lock, or a screw (not shown).

In the fifth embodiment of FIGS. 7 and 8, the disposable cartridge 2 further comprises a plane rigid cover plate 12 that is attached to the lower surface 48 of the body 47 of the disposable cartridge 2. The top layer 4 is attached to said rigid cover plate 12, which rigid cover plate 12 comprises through holes 19 that are located at the loading sites 41 (here at the piercing site 41' and at the capillary orifice 41") of the top layer 4. The rigid cover plate 12 here provides for a straight attachment surface for the top layer 4 and also comprises the through hole 19. The cover plate may be manufactured from a rigid material like clear Mylar® (trademark of DuPont Teijin; a film from polyethylene terephthalate, PET). The rigid cover may be coated (preferably on the lower side) with an electrically conductive material 15, e.g. from titanium indium oxide (TIO) or from a plastic material with electrically conductive filler materials in order to achieve the function of the cover plate 12 as described before. As indicated with darker lines, the cover plate 12 is attached to the lower surface 48 of the body 47 of the disposable cartridge 2. This attachment may be achieved by the use of an adhesive tape or a glue strip that preferably is from a chemically inert material just like the Mylar. Depending on the material of the body 47 of the cartridge 2, also welding methods can be applied for attaching the cover plate 12 to the cartridge 2. As indicated with darker lines, the top layer 4 here is sealingly attached to the lower surface 48 of cover plate 12. This attachment of the top layer 4 can be carried out by using an adhesive tape or a glue strip, or by welding (e.g. by laser welding). The flexible bottom layer 3 is sealingly attached to the top layer 4 along the circumference 40 of the flexible bottom layer 3 by using an adhesive tape or a glue strip, or by applying a welding technique.

In FIG. 7, a pipetting orifice 41''' is depicted as well. Such pipetting orifices 41''' that are located in the central opening 43 of the disposable cartridge 2 and that are configured to be accessible by a pipette tip can thus be used for pipetting of processing liquids, reagents or samples directly into the gap 6. Of course, the pipetting orifice 41''' comprises an opening in the cover plate 12 (if present) and a through hole in the top layer 4. Such pipetting orifices 41''' can be used in addition to or instead of one or more piecing orifices 41', which in each case are located below a compartment 21.

This disposable cartridge 2 comprises at least one plunger 42 that in each case is configured to be movable within a compartment 21 manually or by an actuating element 38 (see FIG. 8) for pressing the content of the respective compartment 21 against a respective loading site 41 of the top layer 4. The plunger 42 comprises a piercing pin 27 that is configured for piercing the top layer 4 at the respective loading site 41 of the compartment 21. Thus, the plunger 42 is configured for pressing some of the content of the compartment 21 through the piercing site 41' of the top layer 4 and into the gap 6. Alternatively, the plunger 42 is configured for pressing some of the content of the compartment 21 through a capillary orifice 41" of the top layer 4 and into the gap 6. This capillary orifice 41" preferably is sized to exhibit capillary forces that prevent flowing though of aqueous liquids without a pressure being applied with the plunger 42 (see FIG. 9, left side). Thus, the loading sites 41 preferably are selected from a group comprising piercing sites 41', capillary orifices 41", and pipetting orifices 41'''.

In FIG. 9, a section view of a disposable cartridge 2 after reaching its cartridge accommodation site 8 on the electrode array 9 of a digital microfluidics system 1 is shown. The disposable cartridge 2 is configured according to a sixth embodiment and is hold in place by a clamp 37.

In the FIG. 9, the plunger 42 is configured to sealing the compartment 21 against an upper surface 49 of the body 47 of the disposable cartridge 2. Preferably, this sealing is achieved with an O-ring seal 39 around the plunger 42. Alternatively, as shown in the FIGS. 9 and 10, to an upper surface 49 of the body 47 of the disposable cartridge 2 is sealingly applied an elastic layer 44 that is configured to seal at least one of the compartments 21 against said upper surface 49. Preferably, the plunger 42 is attached to the elastic layer 44 with its backside, so without applying any pressure to the outside of the elastic layer (manually or with an actuating element 38, see FIG. 10); the plunger 42 is held in place close to the upper surface 49 of the body 47 (see FIG. 7).

If however, the plunger 42 is pressed down (see FIG. 8 and FIG. 9, on the right), the piercing pin 27 penetrates the through hole 19 in the cover layer 12 or body 47 and pierces the top layer 4. Concurrently, a portion of the content of the compartment 21, be it a processing liquid, a reagent or a sample (in a solution or suspension), is pressed by the plunger into the gap 6. As a result, on the first hydrophobic surface 17' of the bottom layer 3, a droplet 23 is built up and can be manipulated in the gap between this first hydrophobic surface 17' of the bottom layer 3 and the second hydrophobic surface 17" of the top layer 4. Manipulating the droplet 23 is effected by the electrode array 9 of the digital microfluidics system 1 the disposable cartridge 2 is accommodated on.

Alternatively, pressing down the plunger 42 shall force a portion of the contents of the compartment 21, be it a processing liquid, a reagent or a sample (in a solution or suspension), to be moved through the capillary orifice 41" and into the gap 6 (see FIG. 9, left side, where the plunger 42 is ready to move). As a result, on the first hydrophobic surface 17' of the bottom layer 3, a droplet 23 will be built up and can be manipulated in the gap between this first hydrophobic surface 17' of the bottom layer 3 and the second hydrophobic surface 17" of the top layer 4. Again, manipulating the droplet 23 will be effected by the electrode array 9 of the digital microfluidics system 1 the disposable cartridge 2 is accommodated on.

According to the sixth embodiment of FIG. 9, the body 47 of the disposable cartridge 2 is configured as a plate-like structure with an essentially flat lower surface 48, in each case the compartments 21 leading to said lower surface 48 with a through hole 19 at the piercing sites 41' or capillary orifices 41".

In the fifth and sixth embodiment of the disposable cartridge 2 of the present invention, it is one preferred alternative that the flexible bottom layer 3 is configured as a monolayer, or single layer respectively, of a hydrophobic material. According to a second preferred alternative, the flexible bottom layer 3 is configured as a monolayer or single layer of electrically non-conductive material, the upper surface 17 of the flexible bottom layer 3 being treated to be hydrophobic. According to a third preferred alternative, the flexible bottom layer 3 is configured as a laminate comprising a lower layer and a hydrophobic upper layer, the lower layer being electrically conductive or non-conductive. According to another preferred embodiment of the disposable cartridge 2 of the present invention, a dielectric layer 24 is laminated onto the lower surface of the bottom layer 3 (see e.g. FIG. 9); in consequence, the upper surface of the individual electrodes 10 are bare metal and the gasket 36 may be attached to the cartridge 2 or to the PCB 11 or bottom substrate 11.

According to one variant of the fifth and sixth embodiment of the disposable cartridge of the present invention, the disposable cartridge 2 further comprises a gasket 36 that is attached to a lower surface and along a circumference 40 of the flexible bottom layer 3. The gasket 36 thus is defining a particular distance between said first hydrophobic surface 17' and said second hydrophobic surface 17", when the disposable cartridge 2 is placed over an electrode array 9 of a digital microfluidics system 1. This is the case, if said digital microfluidics system 1 is equipped with suction holes 35 in the electrode array 9 or PCB 11, and if the flexible bottom layer 3 is aspirated by said suction holes 35.

FIG. 10 shows a section view of a disposable cartridge 2 after reaching its accommodation site 8, the disposable cartridge 2 being configured according to a seventh embodiment and being hold in place without a clamp. Actually, two different variants of the seventh embodiment are shown:

on the left side, the body 47 is configured as plate structure;
on the right side, the body 47 is configured as frame structure;

with the lower surface 48 of the body 47 of the disposable cartridge 2 in both cases being essentially flat. Thus, the disposable cartridge 2 configured according to the ninth embodiment comprises a body 47 with a lower surface 48, an upper surface 49, and at least one through hole 19. The at least one through hole 19 is designed as a pipetting orifice 41''' that is configured to be accessible by a pipette tip 26. The through hole 19 and thus allows pipetting of processing liquids, reagents or samples into the gap 6.

In addition to the body 47, the disposable cartridge 2 comprises a bottom layer 3 with a first hydrophobic surface 17' that is impermeable to liquids and that is configured as a working film for manipulating samples in liquid droplets 23 thereon. Such manipulating is performed utilizing an electrode array 9 of a digital microfluidics system 1 when the bottom layer 3 of the disposable cartridge 2 is placed over said electrode array 9. Preferably, the flexible bottom layer 3 is sealingly attached to an electrically conductive material 15 along a circumference 40 of the flexible bottom layer 3 by an adhesive tape or a glue strip, or alternatively by welding.

The disposable cartridge 2 preferably further comprises an electrically conductive material 15 attached to the lower surface 48 of the body 47. The electrically conductive material 15 is configured to provide the lower surface 48 of the body 47 with a second hydrophobic surface 17" that at least is permeable to ions. The bottom layer 3 is configured as a flexible film that is sealingly attached to the electrically conductive material 15 of the disposable cartridge 2 along a circumference 40 of the flexible bottom layer 3, the disposable cartridge 2 thus being devoid of a spacer 5 (cv. FIGS. 2, 4, and 6-8) that is located between the flexible bottom layer 3 and the electrically conductive material 15 for defining a particular distance between said first hydrophobic surface 17' and said second hydrophobic surface 17".

The disposable cartridge 2 further comprises a gap 6 that is located between the first hydrophobic surface 17' of the bottom layer 3 and the second hydrophobic surface 17" of the electrically conductive material 15. The at least one through hole 19 of the body 47 is configured as a loading site 41 for transferring processing liquids, reagents or samples into the gap 6.

The disposable cartridge 2 preferably further comprises something like a compartment 21, which is configured as one or more container-like depressions in the body 47 located around one or more loading sites 41. However, these compartments 21 are not meant to store liquids over a long period of time or even during shipping, they are merely configured to allow a pipette tip 26 (disposable or not) to reach near the pipetting orifices 41''' located at the loading sites 41. Preferably, these "compartments 21" comprise a central depression around the loading sites 41, which central depression allows some liquid to be deposited temporarily prior to the transfer of the liquid into the gap 6.

As in all other embodiments previously shown, the flexible bottom layer 3 preferably is configured as a monolayer, or single layer respectively, of a hydrophobic material. According to a first preferred alternative variant, the flexible bottom layer 3 is configured as a monolayer of electrically non-conductive material, an upper surface of the flexible bottom layer 3 being treated to be a hydrophobic surface 17. According to a second preferred alternative variant, the flexible bottom layer 3 is configured as a laminate comprising a lower layer and a hydrophobic upper layer, the lower layer being electrically conductive or non-conductive.

In another alternative embodiment, the disposable cartridge 2 further comprises a gasket 36 that is attached to a lower surface and along a circumference 40 of the flexible bottom layer 3. The gasket 36 thus defining a particular distance between said first hydrophobic surface 17' and said second hydrophobic surface 17", when the disposable cartridge 2 is placed over an electrode array 9 of a digital microfluidics system 1, if said digital microfluidics system 1 is equipped with suction holes 35 in the electrode array 9 or PCB 11, and if the flexible bottom layer 3 is aspirated by said suction holes 35.

In the FIG. 10, the gasket 36 is attached to the bottom substrate 11 or PCB that supports the individual electrodes 10 of the electrode array 9. Here, a dielectric layer 24 is attached to the uppermost surface of the electrode array 9, protecting the individual electrodes from oxidation, mechanical impact and other influences like contamination. The dielectric layer 24 also covers the gasket 36 that is configured as a closed ring that extends around the accommodation site 8 for the disposable cartridge 2. For ease of cleaning, the dielectric layer 24 further covers at least a part of the insertion guide 25 and reaches over a part (see left side) or beyond the entire height of the disposable cartridge 2 (see right side).

According to the fifth, sixth, and seventh embodiment of the of the disposable cartridge 2 of the present invention described so far, it is also proposed a first alternative digital microfluidics system that is configured to take up at least one of these inventive disposable cartridges 2 in its cartridge accommodation sites 8 located on the electrode array 9 of the base unit 7. Such a digital microfluidics system 1 for manipulating samples in liquid droplets within the gap 6 between the flexible bottom layer 3 and the top layer 4 of at least one such disposable cartridge 2 preferably comprises:

(a) a base unit 7 with at least one cartridge accommodation site 8 that is configured for taking up the disposable cartridge 2;
(b) an electrode array 9 located at said cartridge accommodation site 8 of the base unit 7, the electrode array 9 being supported by a bottom substrate 11 and substantially extending in a first plane and comprising a number of individual electrodes 10; and
(c) a central control unit 14 for controlling the selection of the individual electrodes 10 of said electrode array 9 and for providing these electrodes 10 with individual voltage pulses for manipulating liquid droplets within the gap 6 of said cartridge 2 by electrowetting.

The first alternative digital microfluidics system 1 further comprises:

(d) a number of suction holes 35 that penetrate the electrode array 9 and that are distributed over the cartridge accommodation site 8 of the base unit 7;
(e) a vacuum source 33 for establishing an underpressure in an evacuation space 46; and
(f) a number of vacuum lines 34 that link the suction holes 35 to the vacuum source 33.

A "number of vacuum lines" can be interpreted as one or more vacuum lines.

The first alternative digital microfluidics system 1 is characterized in that a gasket 36, when located around a circumference 45 of the cartridge accommodation site 8, seals in the cartridge accommodation site 8 the evacuation space 46, which is defined by the flexible bottom layer 3 of the disposable cartridge 2, the electrode array 9 and the bottom substrate 11 of the digital microfluidics system 1, and the gasket 36.

The first alternative digital microfluidics system 1 is further characterized in that the underpressure in the evacuation space 46 causes the flexible bottom layer 3 of the disposable cartridge 2 that is placed on the cartridge accommodation site 8 to be attracted and spread over the electrode array 9 and bottom substrate 11 or PCB of the digital microfluidics system 1. It is expressly noted that the gap 6 defined by this spreading the flexible bottom layer 3 of the disposable cartridge 2 is enabled without the use of a spacer 5 located between the flexible bottom layer 3 and the top layer 4 of the disposable cartridge 2.

According to another variant of the fifth and sixth embodiment of the disposable cartridge 2 of the present invention, the disposable cartridge 2 does not comprise a gasket 36. Instead, the gasket 36 is permanently fixed to the bottom substrate 11 of the base unit 7 of the digital microfluidics system 1, or the gasket 36 is fixed to a dielectric layer 24 that permanently covers the electrode array 9 and the bottom substrate 11 or PCB. Of course in this case, the dielectric layer 24 has holes at the sites of the suction holes 35 of the base unit 7 in order to enable formation of the underpressure in the evacuation space 46, which causes the flexible bottom layer 3 of the disposable cartridge 2 that is placed on the cartridge accommodation site 8 to be attracted and spread over the electrode array 9 and bottom substrate 11 of the digital microfluidics system 1.

According to a further variant of the fifth and sixth embodiment of the disposable cartridge 2 of the present invention, the gasket 36 is permanently attached to a lower surface and along a circumference 40 of the flexible bottom layer 3 of a disposable cartridge 2 to be placed on the cartridge accommodation site 8 of the base unit 7.

The first alternative digital microfluidics system 1 preferably is equipped with a base unit 7, which comprises an insertion guide 25 that is configured as a frame, which is sized to accommodate a disposable cartridge 2 therein. It is especially preferred that the base unit 7 comprises a clamp 37 that is configured to fix this disposable cartridge 2 at a desired position on the cartridge accommodation site 8 of the base unit 7. As demonstrated in connection with the seventh embodiment (see FIG. 10), there is no absolute need for using such a clamp 37. Here, the layers are all sealed well and the vacuum in the evacuation space 46 on the bottom surface holds the disposable cartridge 2 safely in place and within the cartridge accommodation site 8 of the digital microfluidics system 1.

It is further preferred that the base unit 7 comprises actuating elements 38 that are configured for actuating plungers 42 that in each case are configured to be movable within a compartment 21 of a disposable cartridge 2 that is placed on the cartridge accommodation site 8. Thus, the plungers 42 in each case are configured for pressing the content of the respective compartment 21 into the gap 6 of the disposable cartridge 2 that is located on the cartridge accommodation site 8 of the base unit 7. Preferably, the actuating elements 38 are configured to be motor driven and controlled by the central control unit 14 of the digital microfluidics system 1. The insertion guide 25 preferably is manufactured from aluminum, from another light metal or light alloy, or from stainless steel.

The following materials and dimensions are especially preferred for manufacturing a disposable cartridge 2 of the present invention:

cover plate 12, the gasket 36, and the gap 6 that potentially comprises samples and processing fluids.

FIG. 11B shows a section view of a flexible bottom layer 3 without gasket attached, the gasket 36 being a part of the cartridge accommodation site 8 of a digital microfluidics system 1. This flexible bottom layer 3 is configured to be inserted at a cartridge accommodation site of a digital microfluidics system 1. This flexible bottom layer 3 is intended to be part of a disposable cartridge 2 according to a second variant of the eighth embodiment and is configured to be removed from the cartridge accommodation site 8 in one piece that comprises the flexible bottom layer 3, a plane rigid cover plate 12, the gasket 36, and the gap 6 that potentially comprises samples and processing fluids.

FIG. 12 shows a section view of a flexible bottom layer 3 with or without gasket 36 attached. Both variants of the flexible bottom layer 3, whether it comprises a gasket 36 or not, are configured as a flexible film that is configured to be laid on an uppermost surface 52 of the cartridge accommodation site 8 of the digital microfluidics system 1 and to

TABLE 1

| Part | No. | Material | Dimensions and Shape |
| --- | --- | --- | --- |
| Bottom layer | 3 | Fluorinated ethylene propylene (FEP), Cyclo olefin polymer (COP) | Foil: 8-50 μm |
| Top layer | 4 | Al foil | Foil: 20-100 μm |
| Gap | 6 | — | Height: 0.2-2.0 mm; preferably 0.5 mm |
| Electrodes | 10 | Al; Cu; Au; Pt | Plating: 1.5 × 1.5 mm |
| Cover plate | 12 | Mylar ®; acrylic | Foil, plate: 0.15-1.8 mm; preferably 1.5 mm |
| Electrically conductive material | 15 | Au, Pt, TIO, PP, PA | Layer: 20-100 μm; preferably 50 μm |
| 1$^{st}$ hydrophobic surface | 17' | COP, FEP | Foil: 8-50 μm |
| 2$^{nd}$ hydrophobic surface | 17" | Teflon ® | Spin coating: 5-500 nm; preferably 20 nm |
| Liquid droplet | 23 | — | Volume: 0.1-5 μl |
| Dielectric layer | 24 | Fluorinated ethylene propylene, FEP | Foil or casting: 20-100 μm |
| Insertion guide | 25 | Al; Al/Mg; steel; PTFE | Frame: 5-30 mm |
| Gasket | 36 | Synthetic or natural rubber | Frame: 0.2-2.0 mm; preferably 0.5 mm |
| Seal | 39 | Viton ®, Neoprene ® | O-ring: 5-10 mm; preferably 7 mm |
| Capilllary orifice | 41" | — | Diameter: 0.1-0.5 mm |
| Pipetting orifice | 41''' | — | Diameter: 0.3-3.0 mm |
| Elastic layer | 44 | Synthetic or natural rubber | Foil: 0.5-2.0 mm |
| Body | 47 | Polypropylene, PP | 65 × 85 mm; 6-25 mm |

A disposable cartridge 2 according to an eighth embodiment is presented in the FIGS. 11A to 15B. This disposable cartridge 2 is configured to be assembled at a cartridge accommodation site 8 of a digital microfluidics system 1, and is also configured to be removed from the cartridge accommodation site 8 in one piece. Thus, a disposable cartridge 2 according to this eighth embodiment can be withdrawn from the cartridge accommodation site 8 and further processed or discarded without any danger of contaminating the surroundings or operating personal.

FIG. 11A shows a section view of a flexible bottom layer 3 with attached gasket 36. This flexible bottom layer-gasket combination 3,36 is configured to be inserted at a cartridge accommodation site 8 of a digital microfluidics system 1. This flexible bottom layer-gasket combination 3,36 is intended to be part of a disposable cartridge 2 according to a first variant of the eighth embodiment and is configured to be removed from the cartridge accommodation site 8 in one piece that comprises the flexible bottom layer 3, a plane rigid define (together with a gasket 36 provided and with an uppermost surface 52 of the cartridge accommodation site 8) an evacuation space 46. Both variants of the flexible bottom layer 3 are further configured to be attracted to and spread over the uppermost surface 52 by the underpressure in the evacuation space 46.

A digital microfluidics system 1 for manipulating samples in liquid droplets within the gap 6 between a first hydrophobic surface 17' of a bottom layer 3 and a second hydrophobic surface 17" of at least one disposable cartridge 2 is depicted in FIG. 12.

This digital microfluidics system 1 comprises:
(a) a base unit 7 with at least one cartridge accommodation site 8 that is configured for taking up one disposable cartridge 2;
(b) an electrode array 9 located at said at least one cartridge accommodation site 8 of the base unit 7, the electrode array 9 being supported by a bottom substrate 11 and substantially extending in a first plane and comprising a number of individual electrodes 10; and (c) a central control unit 14 for controlling the selection of the individual electrodes 10 of said electrode array 9 and for providing these electrodes 10 with individual voltage pulses for manipulating liquid droplets within the gap 6 of said cartridge 2 by electrowetting.

This digital microfluidics system 1 further comprises:

(d) a number of suction holes 35 that penetrate the electrode array 9 and/or the bottom substrate 11 and that are located at the cartridge accommodation site 8 of the base unit 7;

(e) a vacuum source 33 for establishing an underpressure in an evacuation space 46; and (f) a number of vacuum lines 34 that link the suction holes 35 to the vacuum source 33.

A "number of vacuum lines" can be interpreted as one or more vacuum lines.

This digital microfluidics system 1 is characterized in that a gasket 36 of the digital microfluidics system 1 or of a disposable cartridge 2 is configured to seal at said cartridge accommodation site 8 the evacuation space 46, which is defined by a flexible bottom layer 3 of a disposable cartridge 2, an uppermost surface 52 of the cartridge accommodation site 8, and the gasket 36.

The digital microfluidics system 1 shown in the FIGS. 12 to 14 comprises a number of suction holes 35 that penetrate the bottom substrate 11, but not the electrode array 9. These suction holes 35 are preferably distributed in the cartridge accommodation site 8 around the area of the electrode array 9. In order to practically evenly distribute the underpressure within the evacuation space 46, the suction holes 35 are configured to mouth into suction channels 51, which suction channels 51 are arranged in the uppermost surface 52 of the cartridge accommodation site 8 of the digital microfluidics system 1. In the embodiment shown in the FIGS. 12 to 14, the uppermost surface 52 of the cartridge accommodation site 8 is provided by the dielectric layer 24 that is attached to the upper surface of the electrode array 9 and the bottom substrate 11. In consequence, the suction channels 51 are configured as grooves that are countersunk in the surface of the dielectric layer 24. The pattern of these suction channels 51 or grooves may comprise branched or un-branched straight lines, branched or un-branched meandering lines and any combinations thereof. As shown, the suction channels 51 or grooves may reach over a part of the electrode array 11 and/or over a part of the bottom substrate 11. Deviating from the straight suction holes 35 as shown in the FIGS. 12 to 14, the suction holes 35 can penetrate the bottom substrate 11 in any arbitrary direction as best suited, e.g. the suction holes 35 can be configured to penetrate the bottom substrate 11 at an oblique angle or stepwise. Especially in a case where the bottom substrate 11 is configured to comprise two separate plates that are sandwiched on top of each other (not shown), stepwise and/or branched configuration of the suction holes 35 may be preferred in order to reduce complexity of the suction channels 51 or grooves in the surface of the dielectric layer 24.

In any case, it is preferred to arrange the suction channels 51 or grooves such that an even underpressure can be established in the evacuation space 46. As soon as the flexible bottom layer 3 of a disposable cartridge 2 is located at the cartridge accommodation site 8, the gasket 36 seals in the cartridge accommodation site 8 the evacuation space 46, which is defined by the flexible bottom layer 3 of the disposable cartridge 2, the uppermost surface 52 of the cartridge accommodation site 8, and the gasket 36.

Preferably, the uppermost surface 52 of the cartridge accommodation site 8 comprises a dielectric layer 24 that covers the electrode array 9 and the bottom substrate 11, the dielectric layer 24 having holes at the sites of the of suction holes 35 of the base unit 7. The suction holes 35 can be directly linked to the vacuum source 33 of the digital microfluidics system 1 by an appropriate number of vacuum lines 34 (see FIGS. 7-10). Preferably, the suction holes 35 may be configured to mouth into a vacuum space 50, which vacuum space 50 is arranged at the at least one cartridge accommodation site 8 and under the electrode array 9 and/or the bottom substrate 11. Preferably, the vacuum space 50 is connected to the vacuum source 33 of the digital microfluidics system 1 by at least one vacuum line 34 (see FIGS. 12 to 14).

This digital microfluidics system 1 is further characterized in that the underpressure in the evacuation space 46 causes the flexible bottom layer 3 that is placed at the cartridge accommodation site 8 to be attracted to and spread over the uppermost surface 52 of the cartridge accommodation site 8 of the digital microfluidics system 1, the gasket 36 defining a particular distance between said first hydrophobic surface 17' and said second hydrophobic surface 17".

Preferably, the gasket 36 is fixed to the dielectric layer 24 that permanently covers the electrode array 9 and the bottom substrate 11 of a cartridge accommodation site 8 of the digital microfluidics system 1. Alternatively, the gasket 36 is permanently fixed to the bottom substrate 11 that supports the electrode array 9; the dielectric layer 24 permanently covering the bottom substrate 11, the electrode array 9, and the gasket 36. As a general alternative, the gasket 36 is fixed to the flexible bottom layer 3 of a prospective disposable cartridge 2.

Preferably, the base unit 7 comprises an insertion guide 25 that is configured as a frame, which is sized to accommodate a disposable cartridge 2 therein. It is further preferred that the base unit 7 comprises a clamp 37 (see FIGS. 13 and 14) that is configured to fix a disposable cartridge 2 at a desired position of a cartridge accommodation site 8 of the base unit 7.

For assembling a disposable cartridge 2 at the cartridge accommodation site 8 of the digital microfluidics system 1, the lower surface 48' of a rigid cover plate 12 (see FIG. 13) and the flexible bottom layer 3 are configured as sealingly attachable to each other along a circumference 40 of the flexible bottom layer 3 by mutual contacting the lower surface 48' of the rigid cover plate 12 and the circumference 40 of the flexible bottom layer 3 that is spread over the uppermost surface 52 of the cartridge accommodation site 8 of the digital microfluidics system 1 (see FIG. 14).

FIG. 13 shows a section view of a flexible bottom layer 3 with or without gasket 36 attached, attracted and spread over the uppermost surface 52 of the cartridge accommodation site 8 of the digital microfluidics system 1 during optional providing of oil 53 onto the first hydrophobic surface 17' of the flexible bottom layer 3. For easy providing the oil 53 to the first hydrophobic surface 17', the rigid cover plate 12 is not in place and an optional clamp is lifted by tilting about a hinge 16 for example.

The oil 53 preferably is applied with pipette 26 and not necessarily covers the entire first hydrophobic surface 17'. In the context of the present invention, any liquid that is immiscible with the sample droplets is called oil 53; it can be silicon oil, hexadecene or any other substance that is liquid at the requested processing temperatures that may e.g. range from below room temperature to almost 100° C. and that is chemically inert with respect to the other processing liquids and samples.

After loading the flexible bottom layer 3 with the appropriate volume of oil 53, a rigid cover plate 12 is laid on the flexible bottom layer 3. Preferably, to an upper surface 49' of the rigid cover plate 12 is sealingly applied a pierceable membrane 31 that is configured to seal at least one of the through holes 19 against said upper surface 49'. It is preferred that to the lower surface 48' of the rigid cover plate 12 is sealingly applied a peel-off protection film 54 that is configured to prevent said lower surface 48' (and the through holes 19 as well) from contamination. If the chosen rigid cover plate 12 comprises such a pierceable membrane 31 and a peel-off protection film 54, preferably only the peel-off protection film 54 is removed and the rigid cover plate 12 carefully placed on the flexible bottom layer 3 and on the oil 53 deposit.

The rigid cover plate 12 may comprise an electrically conductive material 15 in the form of a thin metal plate, metal foil, or metal layer that is attached or deposited to the lower surface 48' of the rigid cover plate 12 and that provides or is treated to provide the second hydrophobic surface 17" that preferably has dielectric properties. Alternatively, the rigid cover plate 12 may comprise or may be built of electrically conductive polymer material 15, the lower surface 48' of the rigid cover plate 12 being treated to provide the second hydrophobic surface 17" that preferably has dielectric properties. Polymers can be made electrically conductive e.g. through addition of carbon particles, carbon nanotubes, carbon fibers, metal particles or metal fibers; however, such polymer products normally are opaque or have at least considerably reduced transparency to visible light. For visually observing droplet manipulation, an opaque electrically conductive polymer material 15 of the rigid cover plate 12 preferably comprises at least one array of optically transparent portions 57. Such transparent portions can e.g. be produced by co-extrusion with the polymer that is rendered electrically conductive. Dielectric property of the lower surface 48' of the rigid cover plate 12 can be achieved by co-extrusion or lamination of a dielectric polymer.

Alternatively, electrically conductive polymers can be selected e.g. from the so-called linear-backbone "polymer blacks" (polyacetylene, polypyrrole, and polyaniline) and their copolymers. By manipulating the band structure, electrically conductive polythiophenes have been modified to make them transparent to visible light. When producing the rigid cover plate 12 from transparent or opaque electrically conductive polymers, dielectric property of the lower surface 48' of the rigid cover plate 12 can be achieved by co-extrusion or lamination of a dielectric polymer.

The gasket 36 may be provided at the cartridge accommodation site 8 as a part of:
(a) the cartridge accommodation site 8 of the digital microfluidics system 1, the gasket 36 being permanently attached to the uppermost surface 52 of the cartridge accommodation site 8 (e.g. to the dielectric layer 24 that forms the uppermost surface 52); or
(b) the flexible bottom layer 3 of the disposable cartridge 2, the gasket 36 being permanently attached to a circumference 40 of the flexible bottom layer 3.

The disposable cartridge 2 is assembled at the cartridge accommodation site 8 of the digital microfluidics system 1 by sealingly attaching the flexible bottom layer 3 to the rigid cover plate 12 along the circumference 40 of the flexible bottom layer 3. Such sealed attachment may be carried out by at least one adhesive tape or glue strip that is located at the circumference 40 of the flexible bottom layer 3 and/or at the lower surface 49' of the rigid cover plate 12. Alternatively, sealed attachment may be achieved by welding, preferably by laser welding.

Preferably, placing a rigid cover plate 12 with a lower surface 48' on the flexible bottom layer 3, contacting said lower surface 48' to and sealingly attaching said lower surface 48' with a circumference 40 of the flexible bottom layer 3 is intensified by pressing the rigid cover plate 12 against the flexible bottom layer 3 utilizing a clamp 37 of the cartridge accommodation site 8. Such a clamp 37 may also be used for holding the cartridge in place at the cartridge accommodation site 8 during manipulating and/or analyzing samples in liquid droplets 23.

FIG. 14 shows a section view of a disposable cartridge 2 as assembled at the cartridge accommodation site 8 of the digital microfluidics system 1, the plane rigid cover plate 12 of the cartridge being pressed to the flexible bottom layer 3 with the assistance of a clamp 37. Because the upper surface 49' of the rigid cover plate 12 has been provided with a pierceable membrane 31 the is not transparent to visible light, the rigid cover plate 12 can be made of opaque material that is electrically conductive (not shown) or that exhibits dielectric properties an that directly provides the second hydrophobic surface 17" as shown. The pierceable membrane 31 is penetrated at the piercing site 41' with a piercing pipette tip 20 and a droplet 23 containing a sample is given to the gap 6 via the through hole 19. After withdrawing the piercing pipette tip 20, manipulation of the droplet may be performed by electrowetting. The parts of the cartridge accommodation site 8 and of the digital microfluidics system 1 are basically the same in the FIGS. 12 to 14 and have been described above.

It is noted here that the clamp 37 may be connected to the insertion guide 25 or any other rigid parts of the digital microfluidics system 1 that are close to the cartridge accommodation site 8. On one side, the clamp 37 preferably is permanently connected to the digital microfluidics system 1 via a hinge 16. On an opposite side, the clamp 37 preferably is temporarily connected to the digital microfluidics system 1 via e.g. a snap lock, a screw or similar feature that may easy be released on request.

The inventive disposable cartridge 2 as depicted in the FIGS. 11 to 15 and the inventive digital microfluidics system 1 as depicted in the FIGS. 12 to 14 enable an alternative method for manipulating samples in liquid droplets 23 that adhere to a hydrophobic surface 17 to be carried out. This alternative method comprises the steps of:
(a) providing a working film in the form of a bottom layer 3 with a first hydrophobic surface 17';
(b) providing a digital microfluidics system 1 with an electrode array 9 that substantially extends in a first plane and that comprises a number of individual electrodes 10 supported by a bottom substrate 11 and connected to a central control unit 14 of the digital microfluidics system 1 for controlling the selection of individual electrodes 10 of said electrode array 9 and for providing these electrodes 10 with individual voltage pulses for manipulating said liquid droplets 23 on said first hydrophobic surface 17' by electrowetting; and
(c) providing a gasket 36 for defining a gap 6 between a second hydrophobic surface 17" of a cartridge 2 and said first hydrophobic surface 17' of the bottom layer 3.

The alternative method is characterized in that it further comprises the steps of:
(d) placing the bottom layer 3 that is configured as a flexible film on an uppermost surface 52 of a cartridge accommodation site 8 of the digital microfluidics system 1 and thereby creating an evacuation space 46 which is defined by said uppermost surface 52, the gasket 36 that also is provided at the cartridge accommodation site 8, and the flexible bottom layer 3;

(e) establishing an underpressure in said evacuation space 46 using a vacuum source 33 that is linked to a number of suction holes 35 which penetrate the electrode array 9 and/or the bottom substrate 11 and which are located at the cartridge accommodation site 8 of a base unit 7 of the digital microfluidics system 1, the gasket 36 sealing the evacuation space 46 and the underpressure in the evacuation space 46 causing the flexible bottom layer 3 to be attracted to and spread over the uppermost surface 52 of the cartridge accommodation site 8 of the digital microfluidics system 1;

(f) adding processing liquids to said first hydrophobic surface 17' of the flexible bottom layer 3;

(g) placing a rigid cover plate 12 with a lower surface 48' on the flexible bottom layer 3, contacting said lower surface 48' to and sealingly attaching said lower surface 48' with a circumference 40 of the flexible bottom layer 3, thereby assembling a disposable cartridge 2 at the cartridge accommodation site 8 of the digital microfluidics system 1, the gasket 36 defining a particular distance between said first hydrophobic surface 17' and said second hydrophobic surface 17"; and (h) adding at least one sample droplet 23 to the gap 6 and manipulating said sample droplet 23 by electrowetting.

After manipulating liquid droplets 23 on the first hydrophobic surface 17' by electrowetting and/or analyzing the sample in some of these liquid droplets 23, the disposable cartridge 2 is taken from the cartridge accommodation site 8 of the base unit 7 of the digital microfluidics system 1 and analyzed or discarded. It is preferred utilizing a pierceable membrane 31 that is attached to the upper surface 49' of the rigid cover plate 12, because this pierceable membrane 31 is sealing the through holes 19 and the gap 6 so that liquids contained in the gap 6 or through holes 19 cannot reach and possibly contaminate the digital microfluidics system 1, the surrounding or the operating personal. This is depicted in the FIG. 15A, which shows a section view of a used disposable cartridge 2 (still containing oil 53 and sample droplets 23 in the gap 6) after removal from the cartridge accommodation site 8 of the digital microfluidics system 1. In this case, the gasket 36 is a part of the flexible bottom layer 3 and in consequence also of the disposable cartridge 2, with which the gasket 36 is disposed.

The rigid cover plate 12 shown in FIG. 15A, as an example is entirely formed of a polymer material that provides dielectric properties. Thus, the lower surface 48' of the rigid cover plate 12 is the second hydrophobic surface 17" that faces the gap 6. In all preferred embodiments, the upper surface of the flexible bottom layer 3 is the first hydrophobic surface 17' that faces the gap 6 as well.

In contrast, FIG. 15B, shows a section view of another example of a used disposable cartridge 2 after removal from the cartridge accommodation site 8 of the digital microfluidics system 1. The difference on the one hand is the fact that the gasket 6 is a part of the digital microfluidics system 1 and stays at the cartridge accommodation site 8 upon removal of the disposable cartridge 2, which still contains oil 53 and sample droplets 23 in the gap 6. The difference on the other hand is that the rigid cover plate 12 comprises opaque polymer material that is electrically conductive. In order to be able to visually control manipulation of liquid droplets 23, the rigid cover plate 12 comprises an array of optically transparent portions 57 that penetrate the rigid cover plate 12. This rigid cover plate 12 preferably comprises a dielectric layer 24 that provides the rigid cover plate 12 with the second hydrophobic surface 17" that faces the gap 6. Because there is no pierceable membrane 31 that would be sealing the through holes 19 and the gap 6, a film seal 55 or a plug 56 are applied here to close the through holes 19 for safe disposal of the used cartridge.

When applying this alternative method, preferably the underpressure in the evacuation space 46 is created by a vacuum source 33, which is controlled by the central control unit 14 of the digital microfluidics system 1, and which is linked by a number of vacuum lines 34 to suction holes 35 that penetrate the electrode array 9 and that are distributed over the cartridge accommodation site 8 of the base unit 7. It is further preferred that a plunger 42 contained in a compartment 21 of the disposable cartridge 2 is moved manually or by an actuating element 38 and the content of the respective compartment 21 is pressed against a respective loading site 41 of the top layer 4. It is also preferred that with a piercing pin 27 of the plunger 42, the top layer 4 is pierced at a respective piercing site 41' of the compartment 21 and some of the content of the compartment 21 is pressed through a hole punched into this piercing site 41' of the top layer 4 and into the gap 6. Alternatively or additionally, it is also preferred that some of the content of the compartment 21 is pressed with the plunger 42 through a respective capillary orifice 41" of the top layer 4 and into the gap 6, the capillary orifice 41" being sized to exhibit capillary forces that prevent flowing though of aqueous liquids without a pressure being applied with the plunger 42.

In each case it is preferred that after manipulating liquid droplets 23 on said first hydrophobic surface 17' by electrowetting and/or analyzing the sample in some of these liquid droplets 23, the disposable cartridge 2 is taken from the cartridge accommodation site 8 of the base unit 7 of the digital microfluidics system 1 and discarded.

Any combination of the features of the different embodiments of the cartridge 2 disclosed herein that appear reasonable to a person of skill are comprised by the gist and scope of the present invention. As a general consequence and depending on the actual design of the digital microfluidics system 1 that is chosen according to the intended use, a dielectric layer 24 may be provided (so that the upper surface of the dielectric layer 24 that points away from the bottom substrate 11 or PCB is configured as the uppermost surface 52 of a cartridge accommodation site 8, see e.g. FIGS. 12-14) or not on top of the individual electrodes 10 of the bottom substrate 11 or PCB respectively. If the bare metal surface of the individual electrodes 10 and the PCB 11 define the uppermost surface 52 of a cartridge accommodation site 8 (see e.g. FIGS. 3 and 9), dielectric property preferably is incorporated in the flexible bottom layer 3 of a disposable cartridge 2 and as a further preference, the suction holes 35 and/or suction channels 51 in the surface of the PCB (if required) may be located in-between the individual electrodes 10.

Even if they are not particularly described in each case, the reference numbers refer to similar elements of the digital microfluidics system 1 and in particular of the disposable cartridge 2 of the present invention.

REFERENCE NUMBERS

| | |
|---|---|
| 1 | digital microfluidics system |
| 2 | disposable cartridge |

| | |
|---|---|
| 3 | flexible bottom layer |
| 4 | top layer |
| 5 | spacer |
| 6 | gap between 3 & 4 or 3 & 12 |
| 7 | base unit |
| 8 | cartridge accommodation site |
| 9 | electrode array |
| 10 | individual electrode |
| 11 | bottom substrate, PCB |
| 12 | cover plate, rigid cover plate |
| 13 | top substrate |
| 14 | central control unit |
| 15 | electrically conductive material |
| 16 | hinge |
| 17 | hydrophobic surface |
| 17' | $1^{st}$ hydrophobic surface |
| 17" | $2^{nd}$ hydrophobic surface |
| 18 | piercing facility |
| 19 | through hole |
| 20 | piercing pipette tip |
| 21 | compartment |
| 22 | additional piercing facility |
| 23 | liquid droplet |
| 24 | dielectric layer |
| 25 | insertion guide |
| 26 | disposable pipette tip, pipette tip |
| 27 | piercing pin |
| 28 | pin plate |
| 29 | displacement portion |
| 30 | closing means |
| 31 | pierceable membrane |
| 32 | separating bar |
| 33 | vacuum source |
| 34 | vacuum line |
| 35 | suction hole |
| 3, 36 | flexible bottom layer - gasket combination |
| 36 | gasket |
| 37 | clamp |
| 38 | actuating element |
| 39 | seal |
| 40 | circumference of 3 |
| 41 | loading site |
| 41' | piercing site |
| 41" | capillary orifice |
| 41''' | pipetting orifice |
| 42 | plunger |
| 43 | central opening |
| 44 | elastic layer |
| 45 | circumference of 8 |
| 46 | evacuation space |
| 47 | body |
| 48 | lower surface of 47 |
| 48' | lower surface of 12 |
| 49 | upper surface of 47 |
| 49' | upper surface of 12 |
| 50 | suction space |
| 51 | suction channels |
| 52 | uppermost surface of 8 |
| 53 | oil |
| 54 | peel-off protection film |
| 55 | film seal |
| 56 | plug |
| 57 | array of optically transparent portions |

What is claimed is:

1. A digital microfluidics system (1) for manipulating samples in liquid droplets within the gap (6) between a first hydrophobic surface (17') of a bottom layer (3) and a second hydrophobic surface (17") of at least one disposable cartridge (2), the digital microfluidics system (1) comprising:
   (a) a base unit (7) with at least one cartridge accommodation site (8) that is configured for taking up one disposable cartridge (2);
   (b) an electrode array (9) located at said at least one cartridge accommodation site (8) of the base unit (7), the electrode array (9) being supported by a bottom substrate (11) and substantially extending in a first plane and comprising a number of individual electrodes (10); and
   (c) a central control unit (14) for controlling the selection of the individual electrodes (10) of said electrode array (9) and for providing these electrodes (10) with individual voltage pulses for manipulating liquid droplets within the gap (6) of said cartridge (2) by electrowetting,
   wherein the digital microfluidics system (1) further comprises:
   (d) a number of suction holes (35) that penetrate the electrode array (9) and/or the bottom substrate (11) and that are located at the cartridge accommodation site (8) of the base unit (7);
   (e) a vacuum source (33) for establishing an underpressure in an evacuation space (46); and
   (f) a number of vacuum lines (34) that link the suction holes (35) to the vacuum source (33);
   wherein a gasket (36) of the digital microfluidics system (1) or of a disposable cartridge (2) is configured to seal at said cartridge accommodation site (8) the evacuation space (46), which is defined by a flexible bottom layer (3) of a disposable cartridge (2), an uppermost surface (52) of the cartridge accommodation site (8), and the gasket (36);
   and wherein the underpressure in the evacuation space (46) causes the flexible bottom layer (3) that is placed at the cartridge accommodation site (8) to be attracted to and spread over the uppermost surface (52) of the cartridge accommodation site (8) of the digital microfluidics system (1), the gasket (36) defining a particular distance between said first hydrophobic surface (17') and said second hydrophobic surface (17").

2. The digital microfluidics system (1) of claim 1, wherein the suction holes (35) are configured to mouth into suction channels (51), said suction channels (51) being arranged in the uppermost surface (52) of the cartridge accommodation site (8) of the digital microfluidics system (1).

3. The digital microfluidics system (1) of claim 1, wherein the suction holes (35) are configured to mouth into a vacuum space (50), said vacuum space (50) being arranged at the cartridge accommodation site (8) and under the electrode array (9) and/or the bottom substrate (11), said vacuum space (50) being connected to the vacuum source (33) of the digital microfluidics system (1) by at least one of the vacuum lines (34).

4. The digital microfluidics system (1) of claim 1, wherein the uppermost surface (52) of the cartridge accommodation site (8) comprises a dielectric layer (24) that covers the electrode array (9) and the bottom substrate (11), the dielectric layer (24) having holes at the sites of the of suction holes (35) of the base unit (7).

5. The digital microfluidics system (1) of claim 4, wherein the gasket (36) is fixed to the dielectric layer (24) that permanently covers the electrode array (9) and the bottom substrate (11) of a cartridge accommodation site (8) of the digital microfluidics system (1).

6. The digital microfluidics system (1) of claim 4, wherein the gasket (36) is permanently fixed to the bottom substrate (11) that supports the electrode array (9); the dielectric layer (24) permanently covering the bottom substrate (11), the electrode array (9), and the gasket (36).

7. The digital microfluidics system (1) of claim 1,
wherein the base unit (7) comprises an insertion guide (25) that is configured as a frame, which is sized to accommodate a disposable cartridge (2) therein.

8. The digital microfluidics system (1) of claim 1, wherein the uppermost surface (52) of the cartridge accommodation site (8) is defined by the bottom substrate (11) and bare metal surfaces of the individual electrodes (10).

9. The digital microfluidics system (1) of claim 1,
wherein the base unit (7) comprises a clamp (37) that is configured to fix a disposable cartridge (2) at a desired position of a cartridge accommodation site (8) of the base unit (7).

10. A disposable cartridge (2) for use in a digital microfluidics system (1) according to claim 1, the disposable cartridge (2) comprising:
(a) a bottom layer (3) with a first hydrophobic surface (17') that is impermeable to liquids and that is configured as a working film for manipulating samples in liquid droplets (23) thereon utilizing an electrode array (9) of the digital microfluidics system (1) when the bottom layer (3) of the disposable cartridge (2) is placed over said electrode array (9);
(b) a plane rigid cover plate (12) comprising a lower surface (48'), at least one through hole (19) located at a loading site (41), and a second hydrophobic surface (17") that is at least permeable to ions; and
(c) a gap (6) that is located between the first hydrophobic surface (17') of the bottom layer (3) and the second hydrophobic surface (17") of the rigid cover plate (12),
wherein the bottom layer (3) is configured as a flexible film that is configured to be laid on an uppermost surface (52) of a cartridge accommodation site (8) of the digital microfluidics system (1) and to be attracted to and spread over said uppermost surface (52) by the underpressure in the evacuation space (46), wherein the disposable cartridge (2) is configured to be assembled at the cartridge accommodation site (8) of the digital microfluidics system (1), the lower surface (48') of the rigid cover plate (12) and the flexible bottom layer (3) being configured as sealingly attachable to each other along a circumference (40) of the flexible bottom layer (3) by mutual contacting the lower surface (48') of the rigid cover plate (12) and the circumference (40) of the flexible bottom layer (3) that is spread over the uppermost surface (52) of the cartridge accommodation site (8) of the digital microfluidics system (1);
and wherein the assembled disposable cartridge (2) is configured to be removed from the cartridge accommodation site (8) in one piece that comprises the bottom layer (3), the plane rigid cover plate (12), and the gap (6) that potentially comprises samples and processing fluids.

11. The disposable cartridge (2) of claim 10,
wherein the flexible bottom layer (3) is configured to be sealingly attached at the cartridge accommodation site (8) of the digital microfluidics system (1) to the rigid cover plate (12) along the circumference (40) of the flexible bottom layer (3):
(i) by at least one adhesive tape or glue strip, or
(ii) by welding.

12. The disposable cartridge (2) of claim 10,
wherein the loading sites (41) are selected from a group comprising piercing sites (41') and pipetting orifices (41''').

13. The disposable cartridge (2) of claim 10,
wherein to an upper surface (49') of the rigid cover plate (12) is sealingly applied a pierceable membrane (31) that is configured to seal at least one of the through holes (19) against said upper surface (49').

14. The disposable cartridge (2) of claim 10,
wherein to the lower surface (48') of the rigid cover plate (12) is sealingly applied a peel-off protection film (54) that is configured to prevent said lower surface (48') from contamination.

15. The disposable cartridge (2) of claim 10,
wherein the rigid cover plate (12) comprises an electrically conductive material (15) in the form of a thin metal plate, metal foil, or metal layer that is attached or deposited to the lower surface (48') of the rigid cover plate (12) and that provides or is treated to provide the second hydrophobic surface (17").

16. The disposable cartridge (2) of claim 10,
wherein the rigid cover plate (12) comprises electrically conductive polymer material (15), the lower surface (48') of the rigid cover plate (12) being treated to provide the second hydrophobic surface (17") that has dielectric properties.

17. The disposable cartridge (2) of claim 16,
wherein the electrically conductive polymer material (15) of the rigid cover plate (12) is opaque and comprises at least one array of optically transparent portions (57) for observing droplet manipulation.

18. The disposable cartridge (2) of claim 10,
wherein the flexible bottom layer (3) is configured as a single layer of a hydrophobic material.

19. The disposable cartridge (2) of claim 10,
wherein the flexible bottom layer (3) is configured as a single layer of electrically non-conductive material, an upper surface of the flexible bottom layer (3) being treated to be a hydrophobic surface (17).

20. The disposable cartridge (2) of claim 10,
wherein the flexible bottom layer (3) is configured as a laminate comprising a lower layer and a hydrophobic upper layer, the lower layer being a dielectric layer (24).

21. The disposable cartridge (2) of claim 10,
wherein the gasket (36) is permanently fixed to a circumference (40) of the flexible bottom layer (3), the assembled disposable cartridge (2) being configured to be removed from the cartridge accommodation site (8) in one piece that comprises the bottom layer (3), the plane rigid cover plate (12), the gasket (36), and the gap (6) that potentially is comprising samples and processing fluids.

22. The disposable cartridge (2) of claim 10,
wherein the gasket (36) is permanently fixed to the digital microfluidics system (2), the assembled disposable cartridge (2) being configured to be removed from the cartridge accommodation site (8) in one piece that comprises the bottom layer (3), the plane rigid cover plate (12), and the gap (6) that potentially is comprising samples and processing fluids.

23. A method for manipulating samples in liquid droplets (23) that adhere to a hydrophobic surface (17) of a working film in a digital microfluidics system (2) or device, the method comprising the steps of:
(a) providing a working film in the form of a bottom layer (3) with a first hydrophobic surface (17');
(b) providing a digital microfluidics system (1) with an electrode array (9) that substantially extends in a first plane and that comprises a number of individual electrodes (10) supported by a bottom substrate (11) and connected to a central control unit (14) of the digital microfluidics system (1) for controlling the selection of individual electrodes (10) of said electrode array (9) and for providing these electrodes (10) with individual voltage pulses for manipulating said liquid droplets (23) on said first hydrophobic surface (17') by electrowetting; and (c) providing a gasket (36) for defining a gap (6) between a second hydrophobic surface (17") of a cartridge (2) and said first hydrophobic surface (17') of the bottom layer (3), wherein the method comprises the steps of:

(d) placing the bottom layer (3) that is configured as a flexible film on an uppermost surface (52) of a cartridge accommodation site (8) of the digital microfluidics system (1) and thereby creating an evacuation space (46) which is defined by said uppermost surface (52), the gasket (36) that also is provided at the cartridge accommodation site (8), and the flexible bottom layer (3);

(e) establishing an underpressure in said evacuation space (46) using a vacuum source (33) that is linked to a number of suction holes (35) which penetrate the electrode array (9) and/or the bottom substrate (11) and which are located at the cartridge accommodation site (8) of a base unit (7) of the digital microfluidics system (1), the gasket (36) sealing the evacuation space (46) and the underpressure in the evacuation space (46) causing the flexible bottom layer (3) to be attracted to and spread over the uppermost surface (52) of the cartridge accommodation site (8) of the digital microfluidics system (1);

(f) adding processing liquids to said first hydrophobic surface (17') of the flexible bottom layer (3);

(g) placing a rigid cover plate (12) with a lower surface (48') on the flexible bottom layer (3), contacting said lower surface (48') to and sealingly attaching said lower surface (48') with a circumference (40) of the flexible bottom layer (3), thereby assembling a disposable cartridge (2) at the cartridge accommodation site (8) of the digital microfluidics system (1), the gasket (36) defining a particular distance between said first hydrophobic surface (17') and said second hydrophobic surface (17"); and (h) adding at least one sample droplet (23) to the gap (6) and manipulating said sample droplet (23) by electrowetting.

24. The method of claim 23,
wherein said gasket (36) is provided at the cartridge accommodation site (8) as a part of:

(a) the cartridge accommodation site (8) of the digital microfluidics system (1), wherein the gasket (36) is permanently attached to:
   (i) a dielectric layer (24) that forms the uppermost surface (52) of the cartridge accommodation site (8); or
   (ii) the bottom substrate (11) that together with bare metal surfaces of individual electrodes (10) form the uppermost surface (52) of the cartridge accommodation site (8); or (b) the flexible bottom layer (3) of the disposable cartridge (2), the gasket (36) being permanently attached to a circumference (40) of the flexible bottom layer (3).

25. The method of claim 23,
wherein placing a rigid cover plate (12) with a lower surface (48') on the flexible bottom layer (3), contacting said lower surface (48') to and sealingly attaching said lower surface (48') with a circumference (40) of the flexible bottom layer (3) is intensified by pressing the rigid cover plate (12) against the flexible bottom layer (3) utilizing a clamp (37) of the cartridge accommodation site (8).

26. The method of claim 23,
wherein adding at least one sample droplet (23) to the gap (6) is carried out by penetrating a pierceable membrane (31) of the disposable cartridge (2) with a piercing pipette tip (20) of a liquid handling system and by dispensing a required volume of a sample liquid into the gap (6).

27. The method of claim 23,
wherein after manipulating liquid droplets (23) on said first hydrophobic surface (17') by electrowetting and/or analyzing the sample in some of these liquid droplets (23), the disposable cartridge (2) is taken from the cartridge accommodation site (8) of the base unit (7) of the digital microfluidics system (1) and analyzed or discarded.

\* \* \* \* \*